US010799485B2

(12) United States Patent
During

(10) Patent No.: US 10,799,485 B2
(45) Date of Patent: *Oct. 13, 2020

(54) METHODS AND COMPOSITIONS FOR TREATMENT OF EPILEPTIC DISORDERS

(71) Applicant: Ovid Therapeutics Inc., New York, NY (US)

(72) Inventor: Matthew During, Weston, CT (US)

(73) Assignee: Ovid Therapeutics Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/789,709

(22) Filed: Feb. 13, 2020

(65) Prior Publication Data
US 2020/0179350 A1 Jun. 11, 2020

Related U.S. Application Data

(63) Continuation of application No. 16/447,300, filed on Jun. 20, 2019, now Pat. No. 10,603,308, which is a continuation of application No. 16/356,517, filed on Mar. 18, 2019, now Pat. No. 10,363,246, which is a continuation of application No. 16/013,500, filed on Jun. 20, 2018, now abandoned, which is a continuation of application No. 15/673,737, filed on Aug. 10, 2017, now abandoned.

(60) Provisional application No. 62/490,293, filed on Apr. 26, 2017, provisional application No. 62/373,589, filed on Aug. 11, 2016.

(51) Int. Cl.
| | |
|---|---|
| A61K 31/437 | (2006.01) |
| A61K 31/57 | (2006.01) |
| A61K 31/5517 | (2006.01) |
| A61K 31/513 | (2006.01) |
| A61K 31/4535 | (2006.01) |
| A61K 31/423 | (2006.01) |
| A61K 31/4192 | (2006.01) |
| A61K 31/36 | (2006.01) |
| A61K 31/27 | (2006.01) |
| A61K 31/19 | (2006.01) |
| A61K 45/06 | (2006.01) |
| A61K 9/00 | (2006.01) |
| A61K 31/197 | (2006.01) |
| A61K 31/4166 | (2006.01) |
| A61K 31/515 | (2006.01) |
| A61K 31/444 | (2006.01) |
| A61K 31/53 | (2006.01) |
| A61K 31/165 | (2006.01) |
| A61K 31/195 | (2006.01) |
| A61K 31/4015 | (2006.01) |
| A61K 31/55 | (2006.01) |
| A61K 31/433 | (2006.01) |
| A61K 31/44 | (2006.01) |
| A61K 31/325 | (2006.01) |
| A61K 31/5513 | (2006.01) |
| A61K 31/7048 | (2006.01) |

(52) U.S. Cl.
CPC .......... *A61K 31/437* (2013.01); *A61K 9/0019* (2013.01); *A61K 31/165* (2013.01); *A61K 31/19* (2013.01); *A61K 31/195* (2013.01); *A61K 31/197* (2013.01); *A61K 31/27* (2013.01); *A61K 31/325* (2013.01); *A61K 31/36* (2013.01); *A61K 31/4015* (2013.01); *A61K 31/4166* (2013.01); *A61K 31/4192* (2013.01); *A61K 31/423* (2013.01); *A61K 31/433* (2013.01); *A61K 31/44* (2013.01); *A61K 31/444* (2013.01); *A61K 31/4535* (2013.01); *A61K 31/513* (2013.01); *A61K 31/515* (2013.01); *A61K 31/53* (2013.01); *A61K 31/55* (2013.01); *A61K 31/5513* (2013.01); *A61K 31/5517* (2013.01); *A61K 31/57* (2013.01); *A61K 31/7048* (2013.01); *A61K 45/06* (2013.01)

(58) Field of Classification Search
CPC .................................................. A61K 31/437
See application file for complete search history.

(56) References Cited

U.S. PATENT DOCUMENTS

| | | | |
|---|---|---|---|
| 8,461,389 B2 | 6/2013 | Regan et al. | |
| 8,618,087 B2 | 12/2013 | Shaw et al. | |
| 9,339,495 B2 | 5/2016 | During | |
| 9,351,968 B1 | 5/2016 | During | |
| 9,399,034 B1 | 7/2016 | During et al. | |
| 9,446,028 B2 | 9/2016 | During | |
| 9,629,853 B2 | 4/2017 | Jones et al. | |
| 9,682,069 B2 | 6/2017 | During | |
| 9,717,716 B2 | 8/2017 | During et al. | |
| 10,071,083 B2 | 9/2018 | During | |
| 10,363,246 B1 * | 7/2019 | During | A61K 31/437 |
| 10,603,308 B2 * | 3/2020 | During | A61K 31/53 |
| 2007/0032553 A1 | 2/2007 | McKeman et al. | |

(Continued)

FOREIGN PATENT DOCUMENTS

| | | |
|---|---|---|
| WO | 2006118897 A1 | 11/2006 |
| WO | 2015189744 A1 | 12/2015 |
| WO | 2016127170 A1 | 8/2016 |

OTHER PUBLICATIONS

Bahi-Buisson et al., Molecular Syndromology, 2011, 2: 137-152.

(Continued)

*Primary Examiner* — Rei Tsang Shiao
(74) *Attorney, Agent, or Firm* — Carter, DeLuca & Farrell LLP

(57) ABSTRACT

Use of allosteric modulators and/or gaboxadol for the treatment of epileptic disorders in a subject in need thereof.

20 Claims, 4 Drawing Sheets

(56) References Cited

U.S. PATENT DOCUMENTS

| | | |
|---|---|---|
| 2007/0112017 A1 | 5/2007 | Barlow et al. |
| 2007/0141161 A1 | 6/2007 | Shaw et al. |
| 2007/0259912 A1 | 11/2007 | Cooper |
| 2011/0034562 A1 | 2/2011 | Regan |
| 2011/0046090 A1 | 2/2011 | Barlow et al. |
| 2011/0172188 A1 | 7/2011 | Mouthon et al. |
| 2012/0035207 A1 | 2/2012 | McKeman et al. |
| 2013/0309306 A1 | 11/2013 | Rogawski et al. |
| 2015/0313913 A1 | 11/2015 | Catterall et al. |
| 2015/0352085 A1 | 12/2015 | During |
| 2016/0038469 A1 | 2/2016 | During |
| 2016/0228418 A1 | 8/2016 | During |
| 2016/0228454 A1 | 8/2016 | Zhang et al. |
| 2017/0014392 A1 | 1/2017 | During |
| 2017/0014393 A1 | 1/2017 | During |
| 2017/0065572 A1 | 3/2017 | During |
| 2017/0348232 A1 | 12/2017 | During |
| 2018/0042903 A1 | 2/2018 | During |
| 2018/0235942 A1 | 8/2018 | During et al. |
| 2018/0344708 A1 | 12/2018 | During |

OTHER PUBLICATIONS

Archer et al., J. of Medical Genetics, 2006, 43(9):729-734.

Deuschl, "Treatment of patients with essential tremor," Lancet Neurol., (2011), vol. 10; pp. 148-161.

Teive, "Essential tremor: phenotypes," Parkinsonism and Related Disorders, 2012 (18S1); pp. S140-S142.

Gironell, "The GABA Hypothesis in Essential Tremor: Lights and Shadows," Tremor and Other Hyperkinetic Movements, (2014), vol. 4; pp. 1-9.

Ebert et al., "Treating Insomnia: Current and Investigational Pharmacological Approaches," Pharmacology & Therapeutics, (2006), vol. 112; pp. 612-629.

James K. Walsh, Ph.D., "Enhancement of Slow Wave Sleep: Implications for Insomnia," Journal of Clinical Sleep Medicine, (2009), Supplement to vol. 5, No. 2; pp. 827-832.

Glykys et al., "The Main Source of Ambient GABA Responsible for Tonic Inhibition in the Mouse Hippocampus," J Physiol, (2007), vol. 582, No. 3; pp. 1163-1178.

Iber et al., "The AASM Manual for the Scoring of Sleep and Associated Events," American Academy of Sleep Medicine (2007); pp. 3-59 (57 pages).

Jennum et al., "Sleep Disorders in Neurodegenerative Disorders and Stroke," European Handbook of Neurological Management, (2011), vol. 1, 2nd Edition, Chapter 39, Section 6—Sleep Disorders, (Ed. Gilhus et al.) Blackwell Publishing Ltd. 2011; pp. 529-543.

Jonas et al., "Neural Inhibition,", Scholarpedia—http://www.scholarpedia.org/article/Neural_inhibition—(2014); 10 pages.

Egawa et al., "Pathophysiological power of improper tonic GABA(A) conductances in mature and immature models." Frontiers in Neural Circuits, Oct. 24, 2013, vol. 7, Article 170; pp. 1-15.

El Idrissi et al., "Decreased GABA(A) receptor expression in the seizure-prone fragile X mouse," Neurosci Lett (2005) vol. 377, No. 3; pp. 141-146.

Hagerman et al., "Treatment of fragile X-associated tremor ataxia syndrome (FXTAS) and related neurological problems", Clinical Intervention in Aging, 2008, vol. 3, No. 2; pp. 251-262.

Lennox-gastaut syndrome; Wikipedia article. dated Jul. 10, 2016; 11 pages.

Natural Patterns of Sleep—Healthy Sleep—(2007) http://healthysleep.med.harvard.edu/healthy/science/what/sleep-patterns-rem-nrem (2007); 3 pages.

Tropea et al., "Partial Reversal of Rett Syndrome-like Symptoms in MeCP2 Mutant Mice," PNAS, Feb. 10, 2009, vol. 106, No. 6; pp. 2029-2034.

Olmos-Serrano et al, "Defective GABAergic Neurotransmission and Pharmacological Rescue of Neuronal Hyperexcitability in the Amygdala in a Mouse Model of Fragile X Syndrome," the Journal of Neuroscience, Jul. 21, 2010, vol. 30, No. 29; pp. 9929-9938(25 pages).

Sarah DeWeerdt, "Fragile X Mice Show Brain-Wave Abnormalities During Sleep," SFARI, Simons Foundation, Autism Research Initiative, Jan. 25, 2013; 2 pages.

Vardya et al., "Positive Modulation of .delta.-Subunit Containing GABAA Receptors in Mouse neurons," Neuropharmacology, (2012), vol. 63; pp. 469-479.

International Search Report and Written Opinion of the International Searching Authority, dated Sep. 27, 2016, corresponding to International Application No. PCT/US16/42238; 8 total pages.

International Search Report and Written Opinion, dated Oct. 4, 2016, corresponding to International Application No. PCT/US16/50702; 9 total pages.

International Search Report and Written Opinion of the International Searching Authority, dated Jul. 18, 2017, corresponding to International Application No. PCT/US17/34443; 5 total pages.

International Search Report and Written Opinion of the International Searching Authority, dated Aug. 26, 2015, corresponding to International Application No. PCT/US15/34018; 12 total pages.

Egawa et al., "Decreased Tonic Inhibition in Cerebellar Granule Cells Causes Motor Dysfunction in a Mouse Model of Angelman Syndrome," Neurodegenerative Disease, Science Translational Medicine, vol. 4, Issue 165 (163ra157), Dec. 5, 2012; pp. 1-10.

Brown et al., "Pharmacological Characterization of a Novel Cell Line Expressing Human .alpha.4.beta.3.delta. GABAA Receptors," British Journal of Pharmacology, (2002), vol. 136, No. 7; pp. 965-974.

International Search Report and Written Opinion of the International Searching Authority, dated Aug. 14, 2015, corresponding to International Application No. PCT/US2015/029155; 19 total pages.

Cao et al., "Clustered burst firing in FMR1 premutation hippocampal neurons: amelioration with allopregnanolone," Human Molecular Genetics, 2012, vol. 21, No. 13, pp. 2923-2935.

Oakley et al., "Synergistic GABA-Enhancing Therapy against Seizures in a Mouse Model of Dravet Syndrome," The Journal of Pharmacology and Experimental Therapeutics, May 2013, vol. 345; pp. 215-224.

International Search Report and Written Opinion of the International Searching Authority, dated Oct. 31, 2017, corresponding to International Patent Application No. PCT/US17/46256; 10 total pages.

Loescher, W., "Development of Tolerance to the Anticonvulsant Effect of GABA-mimetic Drugs in Animal Models of Seizure States in Tolerance to Beneficial and Adverse Effects of Antiepileptic Drugs," Koella et al. (eds.), (1986); pp. 37-45.

Petersen et al., "THIP: A Single Blind Controlled Trial in Patients with Epilepsy," Acta Neurol. Scand. 67; pp. 114-117 (1983).

PCT Notice concerning Transmittal of International Preliminary Report on Patentability (Chapter I of the Patent Cooperation Treaty), International Preliminary Report on Patentability and Written Opinion of the International Searching Authority,dated Feb. 1, 2018, corresponding to International Application No. PCT/US2016/042238; 8 total pages.

Reagan-Shaw et al., "Dose translation from animal to human studies revisited", FASEB J, vol. 22, No. 3, Oct. 17, 2007; pp. 659-661.

International Search Report and Written Opinion of the International Searching Authority, dated Apr. 24, 2018, corresponding to International Application No. PCT/US18/16602; 15 total pages.

Bahi-Buisson et al., "The three stages of epilepsy in patients with CDKL5 mutations", Epilepsia, (2008), vol. 49, No. 6; pp. 1027-1037.

Tenney et al., "The Current State of Absence Epilepsy: Can We Have Your Attention?", Epilepsy Currents, Current Review in Clinical Science, vol. 13, No. 3 (May-Jun. 2013); pp. 135-140.

Bahi-Buisson et al., "CDKL5-Related Disorders: From Clinical Description to Molecular Genetics," Molecular Syndromology, (2011), vol. 2; pp. 137-152.

Monaghan et al., "Initial Human Experience with Ganaxolone, a Neuroactive Steroid with Antiepileptic Activity," Epilepsia, (1997), vol. 38, No. 9; pp. 1026-1031.

(56) References Cited

OTHER PUBLICATIONS

European Search Report dated Nov. 18, 2019, corresponding to European Application No. 19190461.4; 11 pages.
Charles A. Handforth, "GABA Receptor May Present Target for New ET Drug Therapy," Essential Tremor, Jun. 4, 2013; 1 page.
Charles A. Handforth, "A Delta GABA Receptor as a Target for Essential Tremor Therapy," National Institutes of Health, Jun. 10, 2015; 4 pages.

\* cited by examiner

METHODS AND COMPOSITIONS FOR TREATMENT OF EPILEPTIC DISORDERS

CROSS-REFERENCE TO RELATED APPLICATIONS

This application is a continuation application of U.S. patent application Ser. No. 16/447,300, filed Jun. 20, 2019, which is a continuation of U.S. patent application Ser. No. 16/356,517, filed Mar. 18, 2019, which is a continuation of U.S. patent application Ser. No. 16/013,500, filed Jun. 20, 2018, which is a continuation of U.S. patent application Ser. No. 15/673,737, filed Aug. 10, 2017, which claims benefit of and priority to U.S. Provisional Application No. 62/490,293, filed Apr. 26, 2017 and U.S. Provisional Application No. 62/373,589, filed Aug. 11, 2016, and all of which are incorporated herein by reference in their respective entireties.

TECHNICAL FIELD

Methods of using allosteric modulators and/or gaboxadol or pharmaceutically acceptable salts thereof for the treatment of epileptic disorders in a subject in need thereof.

BACKGROUND

Allosteric modulators such as neurosteroids (e.g., ganaxolone, allopregnanolone), benzodiazapines (e.g., diazepam) and potassium channel openers (e.g., ritigabine) have been used in the treatment of epilepsy. However, treatment with these agents is often limited to patients that do not respond to traditional medications. For example, allopregnanolone is currently in development for the treatment of super refractory status epilepticus. In addition, diazepam is currently marketed (Diastat®) for use in emergency situations to stop cluster seizures in people who are taking other medications to treat epilepsy.

Gaboxadol (4,5,6,7-tetrahydroisoxazolo [5,4-c] pyridine-3-ol) (THIP)) is described in EP Patent No. 0000338, in EP Patent No. 0840601, and in U.S. Pat. Nos. 4,278,676, 4,362,731, 4,353,910, and WO 2005/094820. Gaboxadol is a selective $GABA_A$ receptor agonist with a preference for δ-subunit containing $GABA_A$ receptors. In the early 1980's gaboxadol was the subject of a series of pilot studies that tested its efficacy as an analgesic and anxiolytic, as well as a treatment for tardive dyskinesia, Huntington's disease, Alzheimer's disease, and spasticity. In the 1990's gaboxadol moved into late stage development for the treatment of insomnia but failed to show significant effects in sleep onset and sleep maintenance in a three-month efficacy study. Additionally, patients with a history of drug abuse who received gaboxadol experienced a steep increase in psychiatric adverse events. As a result of these negative results the development of gaboxadol was terminated.

Parenteral dosage forms are intended for administration as an injection or infusion. Common injection types are intravenous (into a vein), subcutaneous (under the skin), and intramuscular (into muscle). Infusions typically are given by intravenous route. Parenteral formulations often include excipients to enhance or maintain active ingredient solubility (solubilizers) and/or stability (buffers, antioxidants, chelating agents, cryo- and lyoprotectants). Excipients also are important in parenteral formulations to assure safety (antimicrobial preservatives), minimize pain and irritation upon injection (tonicity agents), and control or prolong drug delivery (polymers). However, excipients may also produce negative effects such as loss of drug solubility, activity, and/or stability.

There remains a need in the art for safe and effective methods and pharmaceutical compositions that provide epileptic treatment. Accordingly, this disclosure provides pharmaceutical compositions and methods that may be used in applications of epileptic disorders, such as status epilepticus.

SUMMARY

Methods are provided for treatment of epileptic disorders including epilepsy, epilepsy with generalized tonic-clonic seizures, epilepsy with myoclonic absences, frontal lobe epilepsy, temporal lobe epilepsy, Landau-Kleffner Syndrome, Ohtahara syndrome, Rasmussen's syndrome, West's syndrome, Lennox-Gastaut syndrome (LGS), Rett syndrome, CDKL5 disorder, childhood absence epilepsy, essential tremor, Dravet syndrome, Doose syndrome, acute repetitive seizures, benign rolandic epilepsy, status epilepticus, refractory status, epilepticus, super-refractory status epilepticus (SRSE), PCDH19 pediatric epilepsy, increased seizure activity or breakthrough seizures (increased seizure activity, also called serial or cluster seizures) and sodium channel protein type 1 subunit alpha (Scn1a)-related disorders by administering to a patient in need thereof a pharmaceutical composition containing an allosteric modulator. Allosteric modulators include one or more of neurosteroids, benzodiazapines, and potassium channel openers. In embodiments, methods of treating epileptic disorders are provided which include administering to a patient in need thereof a pharmaceutical composition including an allosteric modulator in combination with gaboxadol or a pharmaceutically acceptable salt thereof.

Parenteral formulations of gaboxadol or pharmaceutically acceptable salts thereof are provided herein. Methods of treating epileptic disorders, including status epilepticus, with parenteral formulations of gaboxadol or a pharmaceutically acceptable salt thereof are provided. In embodiments, parenteral formulations including gaboxadol or a pharmaceutically acceptable salt thereof, alone or in combination with an allosteric modulator, are administered to a patient in need thereof to treat an epileptic disorder.

In embodiments, methods are provided for treatment of epileptic disorders including status epilepticus, benign rolandic epilepsy (BRE), intractable childhood epilepsy (ICE), childhood absence epilepsy (CAE), juvenile myoclonic epilepsy (JME), infantile spasms (or West syndrome), Dravet syndrome and Lennox-Gastaut syndrome (LGS) by administering to a patient in need thereof a pharmaceutical composition including an allosteric modulator either alone or in combination with gaboxadol or a pharmaceutically acceptable salt thereof. In embodiments, methods are provided for treatment of epileptic disorders including status epilepticus, benign rolandic epilepsy (BRE), intractable childhood epilepsy (ICE), childhood absence epilepsy (CAE), juvenile myoclonic epilepsy (JME), infantile spasms (or West syndrome), Dravet syndrome and Lennox-Gastaut syndrome (LGS) by administering to a patient in need thereof a pharmaceutical composition including gaboxadol or a pharmaceutically acceptable salt thereof either alone or in combination with an allosteric modulator.

In embodiments, methods are provided for treatment of epileptic disorders characterized as a sodium channel protein type 1 subunit alpha (Scn1a)-related disorder. Scn1a-related disorders include generalized epilepsy with febrile seizures plus, intractable childhood epilepsy with generalized tonic-clonic seizures, intractable infantile partial seizures, myoclonic-astatic epilepsy, severe myoclonic epilepsy in infancy, simple febrile seizures, Dravet syndrome, Lennox-Gastaut syndrome (LGS), infantile spasms, and vaccine-related encephalopathy and seizures. In embodiments, methods are provided for treatment of a sodium channel protein type 1 subunit alpha (Scn1a)-related disorder by administering to a patient in need thereof a pharmaceutical composition including an allosteric modulator. In embodiments, methods are provided for treatment of a sodium channel protein type 1 subunit alpha (Scn1a)-related disorder by administering to a patient in need thereof a pharmaceutical composition including an allosteric modulator in combination with gaboxadol or a pharmaceutically acceptable salt thereof. In embodiments, methods are provided for treatment of a sodium channel protein type 1 subunit alpha (Scn1a)-related disorder by administering to a patient in need thereof a pharmaceutical composition including gaboxadol or a pharmaceutically acceptable salt thereof. In embodiments, methods are provided for treatment of a sodium channel protein type 1 subunit alpha (Scn1a)-related disorder by administering to a patient in need thereof a pharmaceutical composition including gaboxadol or a pharmaceutically acceptable salt thereof in combination with an allosteric modulator. In embodiments, methods are provided for treatment of a sodium channel protein type 1 subunit alpha (Scn1a)-related disorder by administering to a patient in need thereof a parenteral formulation including gaboxadol or a pharmaceutically acceptable salt thereof. In embodiments, methods are provided for treatment a sodium channel protein type 1 subunit alpha (Scn1a)-related disorder by administering to a patient in need thereof a pharmaceutical composition including an allosteric modulator in combination with a parenteral formulation including gaboxadol or a pharmaceutically acceptable salt thereof.

In embodiments, a combination of allosteric modulators, e.g., a neurosteroid, benzodiazapine, or potassium channel opener, may be administered to a patient in need thereof. In embodiments, a combination of one or more allosteric modulators and gaboxadol or a pharmaceutically acceptable salt thereof is administered to a patient in need thereof.

DETAILED DESCRIPTION

Figure 1:
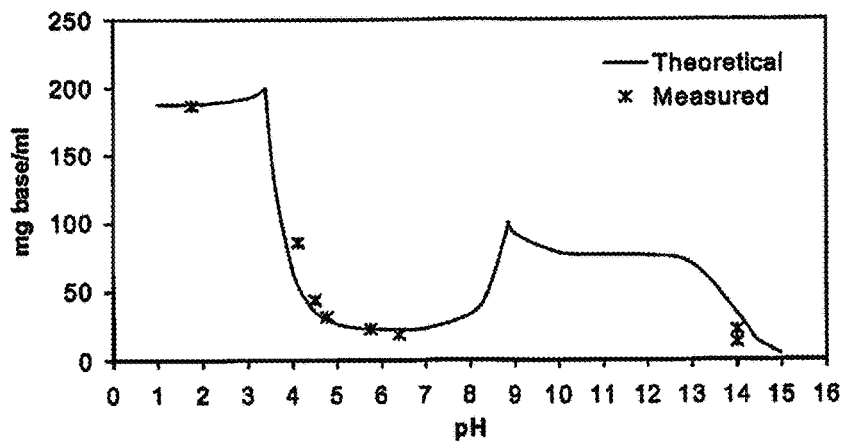
FIG. 1 shows both the theoretical and measured solubility of gaboxadol at different pH values.

Described herein are methods of treating epileptic disorders including epilepsy, epilepsy with generalized tonic-clonic seizures, epilepsy with myoclonic absences, frontal lobe epilepsy, temporal lobe epilepsy, Landau-Kleffner Syndrome, Ohtahara syndrome, Rasmussen's syndrome, infantile spasms (or West syndrome), Lennox-Gastaut syndrome (LGS), Rett syndrome, Dravet syndrome, Doose syndrome, CDKL5 disorder, intractable childhood epilepsy (ICE), childhood absence epilepsy (CAE), juvenile myoclonic epilepsy (JME), essential tremor, acute repetitive seizures, benign rolandic epilepsy, status epilepticus, refractory status, epilepticus, super-refractory status epilepticus (SRSE), PCDH19 pediatric epilepsy, increased seizure activity or breakthrough seizures (increased seizure activity; also called serial or cluster seizures). Compositions and methods described herein may be used to treat epileptic disorders characterized as a sodium channel protein type 1 subunit alpha (Scn1A)-related disorder. For example, Scn1A-related disorders include generalized epilepsy with febrile seizures, intractable childhood epilepsy with generalized tonic-clonic seizures, intractable infantile partial seizures, myoclonic-astatic epilepsy, severe myoclonic epilepsy in infancy, simple febrile seizures, Dravet syndrome, Lennox-Gastaut syndrome, infantile spasms, and vaccine-related encephalopathy and seizures. The compositions and methods described herein involve allosteric modulators and/or gaboxadol or a pharmaceutically acceptable salt thereof.

In embodiments, a method of treating an epileptic disorder may include administering to a patient in need thereof a pharmaceutical composition including an allosteric modulator. In embodiments, a method of treating an epileptic disorder may include administering to a patient in need thereof a pharmaceutical composition including gaboxadol or a pharmaceutically acceptable salt thereof. In embodiments, a method of treating an epileptic disorder may include administering to a patient in need thereof gaboxadol or a pharmaceutically acceptable salt thereof, in combination with an allosteric modulator. In embodiments, a method of treating an epileptic disorder may include administering to a patient in need thereof a parenteral pharmaceutical formulation including an allosteric modulator. In embodiments, a method of treating an epileptic disorder may include administering to a patient in need thereof a parenteral pharmaceutical composition including gaboxadol or a pharmaceutically acceptable salt thereof. In embodiments, a method of treating an epileptic disorder may include administering to a patient in need thereof a parenteral pharmaceutical composition including an allosteric modulator and gaboxadol or a pharmaceutically acceptable salt thereof.

Many pharmaceutical products are administered as a fixed dose, at regular intervals, to achieve therapeutic efficacy. The duration of action is reflected by the product's plasma half-life. Since efficacy is often dependent on sufficient exposure within the central nervous system administration of CNS drugs with a short half-life may require frequent maintenance dosing. Advantageously disclosed herein are methods of treating epileptic disorders by administration of an allosteric modulator. For example, in embodiments, methods of treating an epileptic disorder are provided which include administering to a patient in need thereof a pharmaceutical composition including about 0.05 mg to about 2000 mg of an allosteric modulator wherein the composition provides improvement for more than 6 hours after administration to the patient. Advantageously disclosed herein are methods of treating epileptic disorders by administration of gaboxadol or pharmaceutically acceptable salt thereof. For example, in embodiments, methods of treating an epileptic disorder are provided which include administering to a patient in need thereof a pharmaceutical composition including about 0.05 mg to about 75 mg of gaboxadol or pharmaceutically acceptable salt thereof, wherein the composition provides improvement for more than 6 hours after administration to the patient.

In embodiments, methods of treating an epileptic disorder include administering to a patient in need thereof a pharmaceutical composition including about 0.05 mg to about 50 mg gaboxadol or a pharmaceutically acceptable salt thereof. In embodiments, methods of treating a epileptic disorder include administering to a patient in need thereof a pharmaceutical composition including about 0.1 mg to about 30 mg gaboxadol or a pharmaceutically acceptable salt thereof.

For example, dosages may include amounts of gaboxadol or pharmaceutically acceptable salt thereof in the range of about, e.g., 0.05 mg to 50 mg, 1 mg to 30 mg, 1 mg to 20 mg, 1 mg to 15 mg, 0.01 mg to 10 mg, 0.1 mg to 15 mg, 0.1 mg to 30 mg, 0.15 mg to 12.5 mg, or 0.2 mg to 10 mg, with doses of 0.05 mg, 0.1 mg, 0.2 mg, 0.3 mg, 0.4 mg, 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 10 mg, 11 mg, 12 mg, 15 mg, 20 mg, 25 mg, and 30 mg being specific examples of doses.

Typically, dosages of gaboxadol or a pharmaceutically acceptable salt thereof are administered once or twice daily to a patient in need thereof. The methods and compositions described herein may provide reduced dosing frequency and reduced adverse events and/or increased efficacy. In embodiments, the dosage is about, e.g., 0.05-30 mg/day, 0.1-20 mg/day, or 0.2-15 mg/day, or 0.5-10 mg/day, or 0.75-5 mg/day, for example 0.1 mg/day, 0.2 mg/day, 0.5 mg/day, 0.75 mg/day, 1 mg/day, 1.5 mg/day, 2 mg/day, 3 mg/day, 4 mg/day, 5 mg/day, 6 mg/day, 7 mg/day, 8 mg/day, 9 mg/day, 10 mg/day, 11 mg/day, 12 mg/day, 13 mg/day, 14 mg/day, 15 mg/day, 16 mg/day, 17 mg/day, 18 mg/day, 19 mg/day, 20 mg/day, 21 mg/day, 22 mg/day, 23 mg/day, 24 mg/day, 25 mg/day, 26 mg/day, 27 mg/day, 28 mg/day, 29 mg/day, or 30 mg/day. In embodiments, gaboxadol or a pharmaceutically acceptable salt thereof, or a derivative or analogue thereof is administered at doses of 0.2 mg to 1 mg in infants or 1-20 mg in adults, once daily.

In embodiments, the pharmaceutical compositions include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg gaboxadol or a pharmaceutically acceptable salt thereof.

In embodiments, the pharmaceutical compositions include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the pharmaceutical compositions include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the pharmaceutical compositions include 2.5 mg, 5 mg, 7.5 mg, 10 mg, 15 mg, or 20 mg gaboxadol or a pharmaceutically acceptable salt thereof.

In embodiments, the total amount of gaboxadol or pharmaceutically acceptable salt thereof and/or gaboxadol administered to a subject in a 24-hour period is 1 mg to 50 mg. In embodiments, the total amount of gaboxadol or pharmaceutically acceptable salt thereof and/or gaboxadol administered to a subject in a 24-hour period is 1 mg to 20 mg. In embodiments, the total amount of gaboxadol or pharmaceutically acceptable salt thereof and/or gaboxadol administered to a subject in a 24-hour period is 5 mg, 10 mg, 15 mg or 20 mg. In embodiments, the total amount of gaboxadol or a pharmaceutically acceptable salt thereof administered to a subject in a 24-hour period is 1 mg to 50 mg. In embodiments, the subject may be started at a low dose and the dosage is escalated. In this manner, it can be determined if the drug is well tolerated in the subject. Dosages can be lower for children than for adults. In embodiments, a dose of gaboxadol for children can be 0.1 mg/kg to 1 mg/kg.

Allosteric modulators may include a neurosteroid, e.g., ganaxolone or allopregnanolone, a benzodiazepine, e.g., midazolam, clobazam, clonazepam, diazepam, lorazepam, flurazepam, lorazepam etc., or a potassium channel opener, e.g., retigabine or flupirtine.

In embodiments, methods are provided for treating an epileptic disorder by administering ganaxolone to a patient in need thereof. In embodiments, methods are provided for treating an epileptic disorder by administering allopregnanolone to a patient in need thereof. In embodiments methods are provided for treating an epileptic disorder by administering a compound of Formula I:

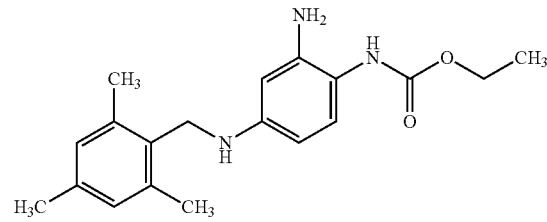

Formula I

In embodiments, an allosteric modulator or a pharmaceutically acceptable salt thereof is administered at dosages ranging from about 0.001 mg/kg to about 30 mg/kg of body weight of a patient in need thereof, e.g., from about 0.01 mg/kg to 20 mg/kg at least once a day. For example, dosages may include amounts of an allosteric modulator or a pharmaceutically acceptable salt thereof in the range of about, e.g., 1 mg to 30 mg, 1 mg to 25 mg, 1 mg to 20 mg, 1 mg to 15 mg, 1 mg to 10 mg, 0.01 mg to 10 mg, 0.1 mg to 15 mg, 0.15 mg to 12.5 mg, or 0.1 mg to 10 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg 28 mg, 29 mg, and 30 mg being specific examples of doses. For example, dosages may include amounts of an allosteric modulator or a pharmaceutically acceptable salt thereof in the range of about, e.g., 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, 975 mg to 1000 mg, 1000 mg to 1025 mg, 1025 mg to 1050 mg, 1050 mg to 1075 mg, 1075 mg to 1100 mg, 1100 mg to 1125 mg, 1125 mg to 1150 mg, 1150 mg to 1175 mg, 1175 mg to 1200 mg, 1200 mg to 1225 mg, 1225 mg to 1250 mg, 1250 mg to 1275 mg, 1275 mg to 1300 mg, 1300 mg to 1325 mg, 1325 mg to 1350 mg, 1350 mg to 1375 mg, 1375 mg to 1400 mg, 1400 mg to 1425 mg, 1425 mg to 1450 mg, 1450 mg to 1475 mg, 1475 mg to 1500 mg, 1500 mg to 1525 mg, 1525 mg to 1550 mg, 1550 mg to 1575 mg, 1575 mg to 1600 mg, 1600 mg to 1625 mg, 1625 mg to 1650 mg, 1650 mg to 1675 mg, 1675 mg to 1700 mg, 1700 mg to 1725 mg, 1725 mg to 1750 mg, 1750 mg to 1775 mg, 1775 mg to 1800 mg, 1800 mg to 1825 mg, 1825 mg to 1850 mg, 1850 mg to 1875 mg, 1875 mg to 1900 mg, 1900 mg to 1925 mg, 1925 mg to 1950 mg, 1950 mg to 1975 mg, or 1975 mg to 2000 mg, of an allosteric modulator.

Typically, dosages of an allosteric modulator or pharmaceutically acceptable salts thereof are administered once daily, twice daily, three times daily or four times daily to a patient in need thereof. In embodiments, allosteric modulators may be administered once weekly. The methods and compositions described herein may provide reduced dosing frequency and reduced adverse events and/or increased efficacy. In embodiments, the dosage of an allosteric modulator can be about, e.g., 0.1-20 mg/day, or 0.2-15 mg/day, or 0.5-10 mg/day, or 0.75-5 mg/day, for example 0.2 mg/day, 0.5 mg/day, 0.75 mg/day, 1 mg/day, 1.5 mg/day, 2 mg/day, 3 mg/day, 4 mg/day, 5 mg/day, 6 mg/day, 7 mg/day, 8 mg/day, 9 mg/day, or 10 mg/day. In embodiments, a patient can be administered an allosteric modulator in an amount of, e.g., 10 mg to 25 mg/day, 25 mg to 50 mg/day, 50 mg to 75 mg/day, 75 mg to 100 mg/day, 100 mg to 125 mg/day, 125 mg to 150 mg/day, 150 mg to 175 mg/day, 175 mg to 200 mg/day, 200 mg to 225 mg/day, 225 mg to 250 mg/day, 250 mg to 275 mg/day, 275 mg to 300 mg/day, 300 mg to 325 mg/day, 325 mg to 350 mg/day, 350 mg to 375 mg/day, 375 mg to 400 mg/day, 400 mg to 425 mg/day, 425 mg to 450 mg/day, 450 mg to 475 mg/day, 475 mg to 500 mg/day, 500 mg to 525 mg/day, 525 mg to 550 mg/day, 550 mg to 575 mg/day, 575 mg to 600 mg/day, 600 mg to 625 mg/day, 625 mg to 650 mg/day, 650 mg to 675 mg/day, 675 mg to 700 mg/day, 700 mg to 725 mg/day, 725 mg to 750 mg/day, 750 mg to 775 mg/day, 775 mg to 800 mg/day, 800 mg to 825 mg/day, 825 mg to 850 mg/day, 850 mg to 875 mg/day, 875 mg to 900 mg/day, 900 mg to 925 mg/day, 925 mg to 950 mg/day, 950 mg to 975 mg/day, 975 mg to 1000 mg/day, 1000 mg to 1025 mg/day, 1025 mg to 1050 mg/day, 1050 mg to 1075 mg/day, 1075 mg to 1100 mg/day, 1100 mg to 1125 mg/day, 1125 mg to 1150 mg/day, 1150 mg to 1175 mg/day, 1175 mg to 1200 mg/day, 1200 mg to 1225 mg/day, 1225 mg to 1250 mg/day, 1250 mg to 1275 mg/day, 1275 mg to 1300 mg/day, 1300 mg to 1325 mg/day, 1325 mg to 1350 mg/day, 1350 mg to 1375 mg/day, 1375 mg to 1400 mg/day, 1400 mg to 1425 mg/day, 1425 mg to 1450 mg/day, 1450 mg to 1475 mg/day, 1475 mg to 1500 mg/day, 1500 mg to 1525 mg/day, 1525 mg to 1550 mg/day, 1550 mg to 1575 mg/day, 1575 mg to 1600 mg/day, 1600 mg to 1625 mg/day, 1625 mg to 1650 mg/day, 1650 mg to 1675 mg/day, 1675 mg to 1700 mg/day, 1700 mg to 1725 mg/day, 1725 mg to 1750 mg/day, 1750 mg to 1775 mg/day, 1775 mg to 1800 mg/day, 1800 mg to 1825 mg/day, 1825 mg to 1850 mg/day, 1850 mg to 1875 mg/day, 1875 mg to 1900 mg/day, 1900 mg to 1925 mg/day, 1925 mg to 1950 mg/day, 1950 mg to 1975 mg/day, or 1975 mg to 2000 mg/day. In embodiments, an allosteric modulator, or a derivative or analogue thereof can be administered at doses of 0.2 mg to 1 mg in infants or 1-20 mg in adults, once daily.

In embodiments, a method of treating an epileptic disorder such as status epilepticus includes administering ganaxolone or a pharmaceutically acceptable salt thereof to a patient in need thereof. Ganaxolone or a pharmaceutically acceptable salt thereof can be administered in doses ranging from 10 mg/kg to 40 mg/kg, e.g., 11 mg/kg to 39 mg/kg, 12 mg/kg to 38 mg/kg, 13 mg/kg to 37 mg/kg, 14 mg/kg to 36 mg/kg, 15 mg/kg to 35 mg/kg, 16 mg/kg to 34 mg/kg, 17 mg/kg to 33 mg/kg, 18 mg/kg to 32 mg/kg, 19 mg/kg to 31 mg/kg, 20 mg/kg to 30 mg/kg, 21 mg/kg to 29 mg/kg, 22 mg/kg to 28 mg/kg, 23 mg/kg to 27 mg/kg, or 24 mg/kg to 26 mg/kg. In embodiments, ganaxolone doses can be, e.g., 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, 1800 mg, 1825 mg, 1850 mg, 1875 mg, 1900 mg, 1925 mg, 1950 mg, 1975 mg, or 2000 mg.

Ganaxolone or a pharmaceutically acceptable salt thereof can be administered, e.g., once daily, twice daily, three times daily, or four times daily. In embodiments, ganaxolone or a pharmaceutically acceptable salt thereof can be administered once weekly. In embodiments, ganaxolone or a pharmaceutically acceptable salt thereof can be administered parenterally as soon as possible after the onset of seizures. In embodiments, ganaxolone or a pharmaceutically acceptable salt thereof can be administered parenterally in escalating doses as soon as possible after the onset of seizures.

In embodiments, a method of treating an epileptic disorder such as status epilepticus includes administering allopregnanolone or a pharmaceutically acceptable salt thereof to a patient in need thereof. Allopregnanolone or a pharmaceutically acceptable salt thereof can be administered in doses ranging, e.g., from 0.01 mg/kg to 20 mg/kg, 0.02 mg/kg to 19 mg/kg, 0.03 mg/kg to 18 mg/kg, 0.04 mg/kg to 17 mg/kg, 0.05 mg/kg to 16 mg/kg, 0.06 mg/kg to 15 mg/kg, 0.07 mg/kg to 14 mg/kg, 0.08 mg/kg to 14 mg/kg, 0.09 mg/kg to 13 mg/kg, 0.1 mg/kg to 12 mg/kg, 0.2 mg/kg to 11 mg/kg, 0.3 mg/kg to 10 mg/kg, 0.4 mg/kg to 9 mg/kg, 0.5 mg/kg to 8 mg/kg, 0.6 mg/kg to 7 mg/kg, 0.7 mg/kg to 6 mg/kg, 0.8 mg/kg to 5 mg/kg, 0.9 mg/kg to 4 mg/kg, or 1 mg/kg to 3 mg/kg. In embodiments, allopregnanolone doses can be, e.g., 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg.

Allopregnanolone or a pharmaceutically acceptable salt thereof can be administered, e.g., once daily, twice daily, three times daily, or four times daily. In embodiments, allopregnanolone or a pharmaceutically acceptable salt thereof can be administered once weekly. In embodiments, allopregnanolone or a pharmaceutically acceptable salt thereof can be administered parenterally as soon as possible after the onset of seizures. In embodiments, allopregnanolone or a pharmaceutically acceptable salt thereof can be administered parenterally in escalating doses as soon as possible after the onset of seizures.

Methods of treating epileptic disorders by administering to a subject in need thereof an effective amount of gaboxadol or a pharmaceutically acceptable salt thereof, either alone or in combination with, an allosteric modulator or a pharmaceutically acceptable salt, derivative or analogue, or combination thereof, are provided. Methods of treating epileptic disorders by administering to a subject in need thereof an effective amount of an allosteric modulator or a pharmaceutically acceptable salt, derivative or analogue, or combination thereof, either alone or in combination with, gaboxadol or a pharmaceutically acceptable salt thereof, are provided.

An effective amount or therapeutically effective amount can be a dosage sufficient to treat, inhibit, or alleviate one or more symptoms of an epileptic disorder such as reducing the frequency or severity of seizures, reducing behavior abnormalities (or otherwise improving behavior); or to provide a desired pharmacologic and/or physiologic effect, for example, reducing, inhibiting, or reversing one or more of the underlying pathophysiological mechanisms underlying the neurological dysfunction, increasing dopamine levels or signaling, or a combination thereof. The precise dosage will vary according to a variety of factors such as subject-dependent variables (e.g., age, immune system health, clinical symptoms etc.). In embodiments, a subject may be started at a low dose and the dosage is escalated. In this manner, it can be determined if the drug is well tolerated in the subject. Dosages can be lower for children than for adults.

In embodiments, the methods described herein are effective to reduce, delay, or prevent one or more other clinical symptoms of an epileptic disorder, such as acute repetitive seizures. For example, the effect of a gaboxadol or a pharmaceutically acceptable salt thereof, and/or an allosteric modulator or a pharmaceutically acceptable salt, derivative or analogue thereof, on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is known the art.

In embodiments, compositions and methods of treatment are provided with low dosages of gaboxadol and/or an allosteric modulator such that the patient is provided one or more beneficial effects related to an epileptic disorder, such as, reduced seizure activity, reduced fatigue, increased mood, increased concentration, increased behavioral control and/or increased cognitive ability. Provided herein are dosing regimens that allow effective treatment of an epileptic disorder with potentially limited or substantially few negative side effects, e.g., convulsions and/or sleep disruption. Accordingly, the methods described herein may provide treatment of an epileptic disorder that may be considered surprising and unexpected. For example, methods are provided herein of treating epileptic disorders in a patient in need thereof which may not cause sleep disruption. In embodiments, methods described herein may provide effective treatment of an epileptic disorder without interrupting Slow Wave Sleep. In embodiments, methods of treating an epileptic disorder without causing insomnia or trouble falling asleep are provided.

In embodiments, the methods described herein may be used to treat epileptic disorders including acute repetitive seizures, Landau-Kleffner Syndrome, Lennox-Gastaut syndrome (LGS) and Dravet syndrome. In embodiments, the methods include treatment of acute repetitive seizure.

In embodiments, the methods described herein may be used to treat epileptic disorders including benign rolandic epilepsy (BRE), intractable childhood epilepsy (ICE), childhood absence epilepsy (CAE), juvenile myoclonic epilepsy (JME), infantile spasms (or West syndrome), generalized epilepsy with febrile seizure plus (GEFS+) and Lennox-Gastaut syndrome (LGS).

In embodiments, the methods described herein may be used to treat a sodium channel protein type 1 subunit alpha (Scn1A)-related disorder. For example Scn1A-related disorders include generalized epilepsy with febrile seizures plus, intractable childhood epilepsy with generalized tonic-clonic seizures, intractable infantile partial seizures, myoclonic-astatic epilepsy, severe myoclonic epilepsy in infancy, simple febrile seizures, Dravet syndrome, Lennox-Gastaut syndrome (LGS), infantile spasms, and vaccine-related encephalopathy and seizures.

The methods described herein may also be effective in subjects experiencing intractable seizures, status epilepticus, akinetic seizures, myoclonic seizures, absence seizures, or severe myoclonic epilepsy in infancy (SMEI). In embodiments, the disorders are characterized by intractable seizures. Intractable seizures (also referred to as "uncontrolled" or "refractory" seizures) are seizures that cannot be controlled with conventional treatments. For example, the subject can have intractable epilepsy or another disorder characterized by intractable seizures, or a disorder characterized by status epilepticus. Status epilepticus is a condition in which seizures follow one another without recovery of consciousness between them. Accordingly, in embodiments, the disclosed methods are used to treat subjects that would otherwise be resistant to one or more conventional therapies.

The methods described herein may be particularly useful for treating children and infants, and for treating disorders that onset during infancy or childhood. In embodiments, the subject of the disclosed method is a newborn, a baby, a toddler, a preschooler, a school-age child, a tween, or a teenager. In embodiments, the subject is 18 years old or younger, 12 years old or younger, 10 years old or younger, 8 years old or younger, 6 years old or younger, 4 years old or younger, 2 years old or younger, 1 year old or younger. In embodiments, the subject is an adult that is over eighteen years old.

In embodiments, the epileptic disorders are characterized by seizures associated with epilepsy. In embodiments, the seizures are non-epileptic seizures (NES) or dissociative seizures that are distinguished from epilepsy. Non-epileptic seizures include organic non-epileptic seizures and psychogenic seizures.

Epilepsy is a neurological disorder that occurs when nerve cell activity in the brain becomes disrupted, leading to seizures or periods of unusual behavior, sensations and sometimes loss of consciousness. A subject can be said to have epilepsy when having two seizures without an obvious cause. Epilepsy can occur in both adults and children, and can be associated with a specific syndrome. Accordingly, in embodiments, the subject has a childhood epilepsy syndrome such as benign rolandic epilepsy (BRE), childhood absence epilepsy (CAE), juvenile myoclonic epilepsy (JME), infantile spasms (or West syndrome), Dravet syndrome or Lennox-Gastaut syndrome (LGS).

In embodiments, the subject does not experience diagnosable seizures, but exhibits subclinical electrical discharges, which refers to a high rate of seizure-like activity when their brain waves are measured with an electroencephalogram. Epileptic syndromes associated with these seizure-like discharges include Landau-Kleffner Syndrome, Dravet syndrome and Continuous Spike-wave Activity during Slow-wave Sleep.

In embodiments, the epileptic disorders treated by the methods and compositions described herein include Scn1A-related seizure disorders. Scn1A-related seizure disorders include simple febrile seizures (FS) and generalized epilepsy with febrile seizures plus (GEFS+) at the mild end to Dravet syndrome and intractable childhood epilepsy with generalized tonic-clonic seizures (ICE-GTC) at the severe end. Specific Scn1A-related seizure disorders include, but are not limited to, generalized epilepsy with febrile seizures, intractable childhood epilepsy with generalized tonic-clonic seizures, intractable infantile partial seizures, myoclonic-astatic epilepsy, severe myoclonic epilepsy in infancy, simple febrile seizures, Dravet syndrome, Lennox-Gastaut syndrome (LGS), infantile spasms, and vaccine-related encephalopathy.

In embodiments, the subject has an intellectual epileptic disability (IDD) such as an Autism Spectrum Disorders (ASD). In embodiments, the subject of the disclosed method has epilepsy and an IDD or ASD disorder. Common IDD and ASD that are comorbid with seizures and epilepsy include, but are not limited to, fragile X syndrome (FXS), Rett syndrome (RTT), Angelman syndrome, Prader-Willi syndrome, Velocardiofacial syndrome, Smith-Lemli-Opitz syndrome, neuroligin mutations and "interneuronopathies" resulting from aristaless-related homeobox, X-linked (ARX) and Nueropilin 2 (NRP2) gene mutations.

Also provided herein are methods and compositions for treating epileptic disorders by co-administering to a patient in need thereof an allosteric modulator, and gaboxadol, a derivative thereof, or a pharmaceutically acceptable salt thereof. In embodiments, the methods and compositions described herein include a dosage form including gaboxadol or a pharmaceutically acceptable salt thereof, and an allosteric modulator. In embodiments, the methods and compositions described herein can include a dosage form including gaboxadol or a pharmaceutically acceptable salt thereof, and a separate dosage form including an allosteric modulator or a pharmaceutically acceptable salt thereof.

Gaboxadol or pharmaceutically acceptable salt thereof may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

In embodiments, gaboxadol is provided as gaboxadol monohydrate. One skilled in the art will readily understand that the amounts of active ingredient in a pharmaceutical composition will depend on the form of gaboxadol provided. For example, pharmaceutical compositions of including 5.0, 10.0, or 15.0 mg gaboxadol correspond to 5.6, 11.3, or 16.9 mg gaboxadol monohydrate.

In embodiments, gaboxadol is crystalline, such as the crystalline hydrochloric acid salt, the crystalline hydrobromic acid salt, or the crystalline zwitter ion monohydrate. In embodiments, gaboxadol is provided as a crystalline monohydrate.

Deuteration of pharmaceuticals to improve pharmacokinetics (PK), pharmacodynamics (PD), and toxicity profiles, has been demonstrated previously with some classes of drugs. Accordingly the use of deuterium enriched gaboxadol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched gaboxadol. See Journal of Labeled Compounds and Radiopharmaceuticals 19(5) 689-702 (1982).

Pharmaceutical compositions herein may be provided with immediate release, delayed release, extended release, or modified release profiles. In embodiments, pharmaceutical compositions with different drug release profiles may be combined to create a two phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions.

In embodiments, the pharmaceutical compositions described herein are administered once, twice, three times or four times daily, or every other day. In embodiments, a pharmaceutical composition described herein is provided to the patient in the evening. In embodiments, a pharmaceutical composition described herein is provided to the patient once in the evening and once in the morning. In embodiments, a pharmaceutical composition herein is provided as soon as possible after the occurrence of a seizure. In embodiments, a pharmaceutical composition herein is provided continuously.

In embodiments, the total amount of allosteric modulator and/or gaboxadol administered to a subject in a 24-hour period is 1 mg to 50 mg. In embodiments, the total amount of allosteric modulator and/or gaboxadol administered to a subject in a 24-hour period is 1 mg to 20 mg. In embodiments, the total amount of allosteric modulator and/or gaboxadol administered to a subject in a 24-hour period is 5 mg, 10 mg, or 15 mg. In embodiments, the total amount of allosteric modulator and/or gaboxadol or a pharmaceutically acceptable salt thereof administered to a subject in a 24-hour period is 1 mg to 50 mg. In embodiments, the subject may be started at a low dose and the dosage is escalated. In this manner, it can be determined if the drug is well tolerated in the subject. Dosages can be lower for children than for adults.

In embodiments, provided herein are methods of treating an epileptic disorder including administering to a patient in need thereof a pharmaceutical composition including an allosteric modulator and/or gaboxadol wherein the composition provides improvement in at least one symptom of the epileptic disorder. In embodiments, methods of treating epileptic disorders by administering to a subject in need thereof an effective amount of allosteric modulator and/or gaboxadol, or combination thereof, are provided. An effective amount or therapeutically effective amount can be a dosage sufficient to treat, inhibit, or alleviate one or more symptoms of an epileptic disorder such as reducing the frequency or severity of seizures, reducing behavior abnormalities (or otherwise improving behavior); or to provide a desired pharmacologic and/or physiologic effect, for example, reducing, inhibiting, or reversing one or more of the underlying pathophysiological mechanisms underlying the neurological dysfunction, increasing dopamine levels or signaling, or a combination thereof. The precise dosage will vary according to a variety of factors such as subject-dependent variables (e.g., age, immune system health, clinical symptoms etc.).

In embodiments, the methods described herein are effective to reduce, delay, or prevent one or more other clinical symptoms of an epileptic disorder, e.g., epilepsy or Dravet syndrome. For example, the effect of a composition including allosteric modulator and/or gaboxadol on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is known the art.

In embodiments, provided herein are methods of treating an epileptic disorder, e.g., status epilepticus, including administering to a patient in need thereof a pharmaceutical composition including an allosteric modulator and/or gaboxadol or pharmaceutically acceptable salt thereof wherein the composition provides improvement in at least one symptom of the epileptic disorder. In embodiments, the methods provided may also surprisingly and unexpectedly reduce or prevent seizures, or symptoms thereof in a subject in need thereof. In embodiments, the methods provided may reduce or prevent one or more different types of seizures. In embodiments, the methods provided may also surprisingly and unexpectedly reduce or prevent seizures, or symptoms thereof in a subject in need thereof. In embodiments, the methods provided may reduce or prevent one or more different types of seizures. Generally, a seizure can include convulsions, repetitive movements, unusual sensations, and combinations thereof. Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures.

In embodiments, methods described herein may reduce the frequency of seizures, reduce the severity of seizures, change the type of seizures (e.g., from a more severe type to a less severe type), or a combination thereof in a subject after treatment compared to the absence of treatment (e.g., before treatment), or compared to treatment with an alternative conventional treatment.

In embodiments, provided herein are methods of treating an epileptic disorder wherein the patient is provided improvement of at least one symptom for more than 4 hours after administration of the pharmaceutical composition to the patient. In embodiments, the improvement of at least one symptom for more than 6 hours after administration of the pharmaceutical composition to the patient is provided in accordance with the present disclosure. In embodiments, improvement of at least one symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one symptom for 12 hours after administration of the pharmaceutical composition to the patient is provided in accordance with the present disclosure.

In embodiments, provided herein methods of treating an epileptic disorder including administering a composition herein to a patient in need thereof wherein the composition provides improvement in next day functioning to the patient.

In embodiments, provided herein are methods of treating an epileptic disorder wherein the amount of active substance, e.g., allosteric modulator and/or gaboxadol, within the patient about 4 hours after administration of the pharmaceutical composition is less than about 75% of the administered dose. In embodiments, provided herein are methods wherein the amount of allosteric modulator and/or gaboxadol or pharmaceutically acceptable salt thereof within the patient about, e.g., 6 hours, 8 hours, 10 hours, 12 hours, 15 hours, or 20 hours after administration of the pharmaceutical composition is less than about 75%.

In embodiments, provided herein are methods of treating an epileptic disorder wherein the amount of active substance, e.g., allosteric modulator and/or gaboxadol, within the patient about 4 hours after administration of the pharmaceutical composition is less than about 80% of the administered dose. In embodiments, provided herein are methods wherein the amount of active substance, e.g., allosteric modulator and/or gaboxadol, within the patient about, e.g., 6 hours, 8 hours, 10 hours, 12 hours, 15 hours, or 20 hours after administration of the pharmaceutical composition is less than about 80% of the administered dose.

In embodiments, provided herein are methods of treating an epileptic disorder wherein the amount of active substance, e.g., allosteric modulator and/or gaboxadol, within the patient about 4 hours after administration of the pharmaceutical composition is between about 65% to about 85% of the administered dose. In embodiments, the amount of active substance, e.g., allosteric modulator and/or gaboxadol, within the patient after about, e.g., 6 hours, 8 hours, 10 hours, 12 hours, 15 hours, or 20 hours after administration of the pharmaceutical composition is between about 65% to about 85% of the administered dose.

In embodiments, provided herein are methods of treating an epileptic disorder including administering to a patient in need thereof a pharmaceutical composition including an active substance, e.g., allosteric modulator and/or gaboxadol, wherein the composition provides an in vivo plasma profile having a $C_{max}$ less than about 500 ng/ml. In embodiments, the composition provides improvement for more than 6 hours after administration to the patient.

In embodiments, the composition provides an in vivo plasma profile having a $C_{max}$ less than about, e.g., 450 ng/ml, 400 ng/ml 350 ng/ml, or 300 ng/ml and wherein the composition provides improvement of next day functioning of the patient. In embodiments, the composition provides an in vivo plasma profile having a $C_{max}$ less than about, e.g., 250 ng/ml, 200 ng/ml 150 ng/ml, or 100 ng/ml and wherein the composition provides improvement of next day functioning of the patient.

In embodiments, provided herein are methods of treating an epileptic disorder including administering to a patient in need thereof a pharmaceutical composition wherein the composition provides a consistent in vivo plasma profile having a $AUC_{0-\infty}$ of less than about 900 ng·hr/ml. In embodiments, the composition provides improvement in next day functioning of the patient. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the composition provides improvement of next day functioning of the patient. In embodiments, the composition provides improvement in one or more symptom for more than 6 hours after administration.

In embodiments, provided herein are methods of treating an epileptic disorder including administering to a patient in need thereof a pharmaceutical composition including an active substance, e.g., allosteric modulator and/or gaboxadol, wherein the composition provides an in vivo plasma profile having a $AUC_{0-\infty}$ of less than about, e.g., 650 ng·hr/ml, 600 ng·hr/ml, 550 ng·hr/ml, 500 ng·hr/ml, or 450 ng·hr/ml. In embodiments, wherein the composition provides an in vivo plasma profile having a $AUC_{0-\infty}$ of less than about, e.g., 400 ng·hr/ml, 350 ng·hr/ml, 300 ng·hr/ml, 250 ng·hr/ml, or 200 ng·hr/ml. In embodiments, the composition provides an in vivo plasma profile having a $AUC_{0-\infty}$ of less than about, e.g., 150 ng·hr/ml, 100 ng·hr/ml, 75 ng·hr/ml, or 50 ng·hr/ml. In embodiments, the composition provides improvement of next day functioning of the patient after administration for more than, e.g., 4 hours, 6 hours, 8 hours, 10 hours, or 12 hours, after administration of the composition to the patient.

In embodiments, provided herein are methods of treating a epileptic disorder including administering to a patient in need thereof a first pharmaceutical composition including gaboxadol or a pharmaceutically acceptable salt thereof and a second pharmaceutical composition including gaboxadol or a pharmaceutically acceptable salt thereof. In some embodiments, the second pharmaceutical composition provides an in vivo plasma profile having a mean $AUC_{0-\infty}$ of at least about 20% less than the first pharmaceutical composition.

In embodiments, provided herein are methods of treating an epileptic disorder including administering to a patient in need thereof a first pharmaceutical composition including an allosteric modulator and a second pharmaceutical composition including gaboxadol or a pharmaceutically acceptable salt thereof. In embodiments, the second pharmaceutical composition provides an in vivo plasma profile having a mean $AUC_{0-\infty}$ of at least about 20% less than the first pharmaceutical composition.

In embodiments, the first and/or the second pharmaceutical compositions are administered once, twice, three or four times daily, or every other day. In embodiments, the first or the second pharmaceutical composition is provided to the patient in the evening. In embodiments, the second pharmaceutical composition includes an amount of gaboxadol that is at least one third of the amount of the allosteric modulator in the first pharmaceutical composition. In embodiments, the second pharmaceutical composition includes an amount of gaboxadol that is at least half of the amount of the amount of the allosteric modulator provided in the first pharmaceutical composition.

In embodiments, the first and/or the second pharmaceutical composition are provided to the patient once in the evening and once in the morning. In embodiments, the total amount of allosteric modulator administered to a subject in a 24-hour period is 1 mg to 2500 mg. In embodiments, the total amount of allosteric modulator administered to a subject in a 24-hour period is 1 mg/kg to 35 mg/kg. In embodiments, the total amount of gaboxadol or a pharmaceutically acceptable salt thereof administered to a subject in a 24-hour period is 1 mg to 75 mg. In embodiments, the total amount of active substance, e.g., gaboxadol or pharmaceutically acceptable salt thereof, administered to a subject in a 24-hour period is less than about 75 mg, 50 mg, 25 mg, 20 mg, 10 mg, or 5 mg. In embodiments, the total amount of active substance, e.g., gaboxadol or pharmaceutically acceptable salt thereof, administered to a subject in a 24-hour period is less than 15 mg. In embodiments, the total amount of active substance, e.g., allosteric modulator and/or gaboxadol, administered to a subject in a 24-hour period is less than about 2500 mg, 2250 mg, 2000 mg, 1750 mg, 1500 mg, 1250 mg, 1000 mg, 750 mg, 500 mg, 250 mg, 200 mg, 175 mg, 150 mg, 125 mg, 100 mg, 75 mg, 50 mg, 25 mg, 20 mg, 10 mg, or 5 mg. In embodiments, the total amount of active substance, e.g., allosteric modulator and/or gaboxadol, administered to a subject in a 24-hour period is less than 15 mg.

In embodiments, the first and/or the second pharmaceutical compositions may be provided with immediate release, delayed release, extended release, or modified release profiles. The first and second pharmaceutical compositions may be provided at the same time or separated by an interval of time, e.g., 6 hours, 12 hours etc. In embodiments, the first and the second pharmaceutical compositions may be provided with different drug release profiles to create a two-phase release profile. For example, the first pharmaceutical composition may be provided with an immediate release profile and the second pharmaceutical composition may provide an extended release profile. In embodiments, one or both of the first and second pharmaceutical compositions may be provided with an extended release or delayed release profile. Such compositions may be provided as pulsatile formulations, multilayer tablets or capsules containing tablets, beads, granules, etc. In some embodiments, the first pharmaceutical composition is an immediate release composition. In embodiments, the second pharmaceutical composition is an immediate release composition. In embodiments, the first and second pharmaceutical compositions are provided as separate immediate release compositions, e.g., tablets or capsules. In embodiments the first and second pharmaceutical compositions are provided 12 hours apart.

In embodiments, compositions described herein are suitable for parenteral administration, including, e.g., intramuscularly (i.m.), intravenously (i.v.), subcutaneously (s.c.), intraperitoneally (i.p.), or intrathecally (i.t.). Parenteral compositions must be sterile for administration by injection, infusion or implantation into the body and may be packaged in either single-dose or multi-dose containers.

In embodiments, liquid pharmaceutical compositions for parenteral administration to a subject include an active substance, e.g., allosteric modulator and/or gaboxadol, at a concentration of about 0.005 µg/ml to about 500 µg/ml. In embodiments, the composition comprises an active substance, e.g., allosteric modulator and/or gaboxadol, at a concentration of, e.g., about 0.005 µg/ml to about 250 µg/ml, about 0.005 µg/ml to about 200 µg/ml, about 0.005 µg/ml to about 150 µg/ml, about 0.005 µg/ml to about 100 µg/ml, or about 0.005 µg/ml to about 50 µg/ml.

In embodiments, the compositions comprises an active substance, e.g., allosteric modulator and/or gaboxadol, at a concentration of, e.g., about 0.05 µg/ml to about 50 µg/ml, about 0.1 µg/ml to about 50 µg/ml, about 0.05 µg/ml to about 25 µg/ml, about 0.05 µg/ml to about 10 µg/ml, about 0.05 µg/ml to about 5 µg/ml, or about 0.05 µg/ml to about 1 µg/ml. In embodiments, the composition comprises an active substance, e.g., allosteric modulator and/or gaboxadol, at a concentration of, e.g., about 0.05 µg/ml to about 15 µg/ml, about 0.5 µg/ml to about 10 µg/ml, about 0.5 µg/ml to about 7 µg/ml, about 1 µg/ml to about 10 µg/ml, about 5 µg/ml to about 10 µg/ml, or about 5 µg/ml to about 15 µg/ml. In embodiments, the pharmaceutical compositions for parenteral administration is formulated as a total volume of about, e.g., 10 ml, 20 ml, 25 ml, 50 ml, 100 ml, 200 ml, 250 ml, or 500 ml. In embodiments, the compositions are contained in a bag, a glass vial, a plastic vial, or a bottle.

In embodiments, compositions for parenteral administration include about 0.05 mg to about 100 mg active substance, e.g., allosteric modulator and/or gaboxadol. In embodiments, the pharmaceutical compositions comprise about, e.g., 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg active substance, e.g., allosteric modulator and/or gaboxadol.

In embodiments, pharmaceutical compositions include about, e.g., 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg active substance, e.g., allosteric modulator and/or gaboxadol. In embodiments, the pharmaceutical compositions include about, e.g., 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg active substance, e.g., allosteric modulator and/or gaboxadol, or amounts that are multiples of such doses. The compositions may be contained in a bag, a glass vial, a plastic vial, or a bottle.

In embodiments, pharmaceutical compositions for parenteral administration to a subject include an active substance, e.g., allosteric modulator and/or gaboxadol, at a concentration of about 0.005 mg/ml to about 500 mg/ml. In embodiments, the compositions include an active substance, e.g., allosteric modulator and/or gaboxadol, at a concentration of, e.g., about 0.05 mg/ml to about 50 mg/ml, about 0.1 mg/ml to about 50 mg/ml, about 0.1 mg/ml to about 10 mg/ml, about 0.05 mg/ml to about 25 mg/ml, about 0.05 mg/ml to about 10 mg/ml, about 0.05 mg/ml to about 5 mg/ml, or about 0.05 mg/ml to about 1 mg/ml. In embodiments, the composition includes an active substance, e.g., allosteric modulator and/or gaboxadol, at a concentration of, e.g., about 0.05 mg/ml to about 15 mg/ml, about 0.5 mg/ml to about 10 mg/ml, about 0.25 mg/ml to about 5 mg/ml, about 0.5 mg/ml to about 7 mg/ml, about 1 mg/ml to about 10 mg/ml, about 5 mg/ml to about 10 mg/ml, or about 5 mg/ml to about 15 mg/ml. In embodiments, pharmaceutical compositions for parenteral administration are formulated as a total volume of about, e.g., 10 ml, 20 ml, 25 ml, 50 ml, 100 ml, 200 ml, 250 ml, or 500 ml. In embodiments, the compositions are packages and stored in a bag, a glass vial, a plastic vial, or a bottle.

In embodiments, pharmaceutical compositions herein include an active substance, e.g., allosteric modulator and/or gaboxadol, wherein the active substance is present at a molarity less than about 1.0 M. In embodiments, the active substance, e.g., allosteric modulator and/or gaboxadol, is present at a molarity greater than, e.g., about 0.0001 M about 0.001 M, about 0.01 M, about 0.1 M, about 0.2 M, greater than about 0.5, greater than about 1.0 M, greater than about 1.2 M, greater than about 1.5 M, greater than about 1.75 M, greater than about 2.0 M, or greater than about 2.5 M. In embodiments, the active substance, e.g., allosteric modulator and/or gaboxadol, is present at a molarity of between, e.g., about 0.00001 M to about 0.1 M, about 0.01 to about 0.1 M, about 0.1 M to about 1.0 M, about 1.0 M to about 5.0 M, or about 5.0 M to about 10.0 M. In embodiments, the active substance, e.g., allosteric modulator and/or gaboxadol, is present at a molarity of less than, e.g., about 0.01 M, about 0.1 M, about 1.0 M, about 5.0 M, or about 10.0 M.

In embodiments, the solubility of the active substance, e.g., allosteric modulator and/or gaboxadol, in the composition is greater than, e.g., about 10 mg/mL, about 15 mg/mL, about 20 mg/mL, about 25 mg/mL, about 30 mg/mL, about 40 mg/mL, about 50 mg/mL, about 75 mg/mL, about 100 mg/mL, about 150 mg/mL, when measured, for example, in water at 25° C.

In embodiments, the solubility of the active substance, e.g., allosteric modulator and/or gaboxadol, in the composition is between, e.g., about 1 mg/mL to about 50 mg/mL, about 5 mg/mL to about 50 mg/mL, about 10 mg/mL to about 50 mg/mL, about 20 mg/mL to about 50 mg/ml, from about 20 mg/mL to about 30 mg/mL or from about 10 mg/mL to about 45 mg/mL, when measured, for example, in water at 25 C.

In embodiments, a pharmaceutical composition for parenteral administration is provided wherein the pharmaceutical composition is stable for at least six months. In embodiments, the pharmaceutical compositions herein exhibit no more than about 5% decrease in active substance, e.g., allosteric modulator and/or gaboxadol, e.g., 3 months or 6 months. In embodiments, the amount of gaboxadol or pharmaceutically acceptable salt thereof degrades at no more than about, e.g., 2.5%, 1%, 0.5% or 0.1%. In embodiments, the degradation is less than about, e.g., 5%, 2.5%, 1%, 0.5%, 0.25%, 0.1%, for at least six months.

In embodiments, pharmaceutical compositions for parenteral administration are provided wherein the pharmaceutical composition remains soluble. In embodiments, pharmaceutical compositions are provided that are stable, soluble, local site compatible and/or ready-to-use. In embodiments, the pharmaceutical compositions herein are ready-to-use for direct administration to a patient in need thereof.

The parenteral compositions provided herein may comprise one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of allosteric modulator and/or gaboxadol or pharmaceutically acceptable salt(s) used in the composition. Thus, parenteral compositions are provided wherein there is no incompatibility between any of the components of the dosage form.

In embodiments, parenteral compositions of allosteric modulator and/or gaboxadol or a pharmaceutically acceptable salt thereof include a stabilizing amount of at least one excipient. For example, excipients may be selected from the group consisting of buffering agents, solubilizing agents, tonicity agents, antioxidants, chelating agents, antimicrobial agents, and preservative. One skilled in the art will appreciate that an excipient may have more than one function and be classified in one or more defined group.

In embodiments, pharmaceutical compositions include an allosteric modulator and/or gaboxadol, or a pharmaceutically acceptable salt thereof and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments pharmaceutical compositions are provided including gaboxadol, or a pharmaceutically acceptable salt thereof, and an excipient wherein the excipient is present in a molar ratio of the excipient to gaboxadol or pharmaceutically acceptable salt of, e.g., about 0.01:1 to about 0.45:1, about 0.1:1 to about 0.15:1, about 0.01:1 to about 0.1:1, and about 0.001:1 to about 0.01:1 are provided. In embodiments, the excipient is present at a molar ratio of the excipient to gaboxadol or pharmaceutically acceptable salt is about 0.0001:1 to about 0.1:1 or about 0.001:1 to about 0.001:1.

In embodiments, pharmaceutical compositions are provided including gaboxadol, or a pharmaceutically acceptable salt thereof and an excipient wherein the excipient comprises a stabilizing amount of a buffering agent. The buffering agent may be used to maintain the pH of the pharmaceutical composition wherein the gaboxadol or pharmaceutically acceptable salt thereof remains soluble, stable, and/or physiologically compatible. For example, in embodiments, the parenteral compositions include a buffering agent wherein the composition remains stable without significant gaboxadol degradation. In embodiments, the addition of a buffer is desired for controlling the pH to enhance stability without significantly catalyzing or degrading the gaboxadol or salt thereof and/or causing pain to the patient upon infusion.

In embodiments, the buffering agent can be a citrate, phosphate, acetate, tartrate, carbonate, glutamate, lactate, succinate, bicarbonate buffer and combinations thereof. For example, sodium citrate, trisodium citrate anhydrous, trisodium citrate dihydrate, sodium citrate dehydrate, triethanolamine (TRIS), trisodium citrate pentahydrate dihydrate (i.e., trisodium citrate dehydrate), acetic acid, citric acid, glutamic acid, phosphoric acid, may be used as a buffering agent. In embodiments, the buffering agent may be an amino acid, alkali metal, or alkaline earth metal buffer. For example, the buffering agent may be sodium acetate or hydrogen phosphate.

In embodiments, parenteral compositions of an active substance, e.g., allosteric modulator and/or gaboxadol are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

In embodiments, pharmaceutical compositions of an active substance, e.g., allosteric modulator and/or gaboxadol, or a pharmaceutically acceptable salt thereof, and an excipient wherein the excipient includes a solubilizing agent. For example, solubilizing agents according to the invention may include, e.g., sodium hydroxide, L-lysine, L-arginine, sodium carbonate, potassium carbonate, sodium phosphate, and/or potassium phosphate. The amount of solubilizing agent in the composition will be sufficient such that the solution remains soluble at all concentrations, i.e., does not turn hazy and/or form precipitates.

In embodiments, provided herein are pharmaceutical compositions of an active substance, e.g., allosteric modulator and/or gaboxadol, or a pharmaceutically acceptable salt thereof, and an excipient wherein the excipient includes a particulate formation inhibitor. A particulate formation inhibitor refers to a compound that has the desired property of inhibiting the formation of particles in parenteral compositions. Particulate formation inhibitors of the invention include ethylenediaminetetraacetic acid (EDTA) and salts thereof, for example, ethylenediaminetetraacetic acid, calcium disodium salt (preferably as the hydrate); ethylenediaminetetraacetic acid, diammonium salt (preferably as the hydrate); ethylenediaminetetraacetic acid, dipotassium salt (preferably as the dihydrate); ethylenediaminetetraacetic acid, disodium salt (preferably as the dihydrate and, if desired, as the anhydrous form); ethylenediaminetetraacetic acid, tetrasodium salt (preferably as the hydrate); ethylenediaminetetraacetic acid, tripotassium salt (preferably as the dihydrate); ethylenediaminetetraacetic acid, trisodium salt (preferably as the hydrate) and ethylenediaminetetraacetic acid disodium salt, USP (preferably as the dihydrate). In embodiments, pharmaceutical compositions described herein have an effective amount of a particulate formation inhibitor. In embodiments the excipients may include, e.g., an amino acid, urea, alcohol, ascorbic acid, phospholipids, proteins, such as serum albumin, collagen, and gelatin; salts such as EDTA or EGTA, and sodium chloride, liposomes, polyvinylpyrollidone, sugars, such as dextran, mannitol, sorbitol, and glycerol, propylene glycol and polyethylene glycol (e.g., PEG-4000, PEG-6000), glycerol, glycine, and/or lipids.

In embodiments, provided herein are pharmaceutical compositions of an active substance, e.g., allosteric modulator and/or gaboxadol, or a pharmaceutically acceptable salt thereof, and an excipient wherein the excipient includes a solubilizing agent. For example, solubilizing agents may include, but are not limited to, acids, such as carboxylic acids, amino acids. In other examples, the solubilizing agents may be saturated carboxylic acids, unsaturated carboxylic acids, fatty acids, keto acids, aromatic carboxylic acids, dicarboxylic acids, tricarboxylic acids, α-hydroxy acids, amino acids, and combinations thereof.

In embodiments, provided herein are pharmaceutical compositions of an active substance, e.g., allosteric modulator and/or gaboxadol, or a pharmaceutically acceptable salt thereof, and an excipient wherein the excipient includes a solubilizing agent such as formic acid, acetic acid, propionic acid, butyric acid, valeric acid, caproic acid, enanthic acid, caprylic acid, pelargonic acid, capric acid, lauric acid, stearic acid, acrylic acid, docosahexaenoic acid, eicosapentaenoic acid, pyruvic acid, benzoic acid, salicylic acid, aldaric acid, oxalic acid, malonic acid, malic acid, succinic acid, glutaric acid, adipic acid, citric acid, lactic acid, alanine, arginine, aspargine, aspartic acid, cysteine, glutamine, glycine, histidine, isoleucine, leucine, lysine, methionine, phenylalanine, praline, serine, threonine, tryptophan, tyrosine, valine, and combinations thereof.

In embodiments, the solubilizing agent is selected from acetic acid, salts thereof, and combinations thereof, (e.g., acetic acid/sodium acetate), citric acid, salts thereof and combinations thereof (e.g., citric acid/sodium citrate), DL arginine, L-arginine and histadine. In embodiments, the solubilizing agent is DL-arginine. In embodiments, the solubilizing agent is L-arginine. In embodiments, the solubilizing agent is acetic acid/sodium acetate. In embodiments, the solubilizing agent is citric acid/sodium citrate.

In embodiments, provided herein are pharmaceutical compositions of an active substance, e.g., allosteric modulator and/or gaboxadol, or a pharmaceutically acceptable salt thereof, and an excipient wherein the excipient renders the composition isotonic. Isotonic pharmaceutical compositions herein may be achieved by adding an appropriate quantity of sodium chloride, glucose, laevulose, dextrose, mannitol, or postassium chloride, or calcium chloride, or calcium gluconoglucoheptonate, or mixtures thereof. For example, the excipients may include one or more tonicity agents, such as, e.g., sodium chloride, potassium chloride, glycerin, mannitol, and/or dextrose. Tonicity agents may be used to minimize tissue damage and irritation, reduce hemolysis of blood cells, and/or prevent electrolyte imbalance. For example, the parenteral compositions may be an aqueous solution including sodium chloride wherein the composition is isotonic. In embodiments, the isotonizing agent is sodium chloride. In embodiments, the concentration of the isotonizing agent is between about 0.01 and about 2.0 weight percent. In embodiments, the pharmaceutical compositions may comprise up to about 10% isotonizing agent. In embodiments the pharmaceutical compositions may comprise up to about, e.g., 0.25%, 0.5%, 1%, 2.5% isotonizing agent. In embodiments the amount of isotonizing agent in the pharmaceutical is between about, e.g., 0.01% to 1%, 0.1% to 1%, 0.25% to 1%, or 0.5% to 1%.

In embodiments, provided herein are pharmaceutical compositions of an active substance, e.g., allosteric modulator and/or gaboxadol, or a pharmaceutically acceptable salt thereof, and an excipient wherein the excipient includes a free radical antagonist. In embodiments, the free radical antagonist is ascorbic acid, ascorbic acid derivatives, organic compounds having at least one thiol, alkyl polyhydroxylated, and cycloalkyl polyhydroxylated compounds, and combinations thereof.

In embodiments, provided herein are pharmaceutical compositions of an active substance, e.g., allosteric modulator and/or gaboxadol, or a pharmaceutically acceptable salt thereof, and an excipient wherein the excipient includes a free radical scavenger selected from thiolyglycolic acid, thiolacetic acid, dithiothreitol, reduced glutathion, thiourea, α-thioglycerol, cystein, aceticystein, mercaptoethane sulfonic acid and combinations thereof.

In embodiments, provided herein are pharmaceutical of an active substance, e.g., allosteric modulator and/or gaboxadol, or a pharmaceutically acceptable salt thereof, and an excipient wherein the excipient includes ribolflavin, dithiothreitol, sodium thiosulfate, thiourea, ascorbic acid, methylene blue, sodium metabisulfite, sodium bisulfite, propyl gallate acetylcysteine, phenol, acetone sodium bisulfate, ascorbic acid, ascorbic acid esters, butylhydroxyanisol (BHA), Butylhydroxytoluene (BHT), cysteine, nordihydroguiaretic acid (NDGA), monothioglycerol, sodium bisulfite, sodium metabisulfate, tocophenols, and/or glutathione.

In embodiments, provided herein are pharmaceutical compositions of an active substance, e.g., allosteric modulator and/or gaboxadol, or a pharmaceutically acceptable salt thereof, and an excipient wherein the excipient includes a preservative. In embodiments, the preservative is selected from benzalkonium chloride, benzethonium chloride, benzyl alcohol, chlorobutanol, chlorocresol, metacresol, Phenol, phenylmercuric nitrate, phenylmercuric acetate, methyl p-hydroxybenzoate, propyl p-hydroxybenzoate, butyl p-hydroxybenzoate, and thimerosal. In other embodiments, the preservative is selected from the group consisting of phenol, meta-cresol, benzyl alcohol, parabens (e.g., methyl, propyl, butyl), benzalkonium chloride, chlorobutanol, thimerosal, phenylmercuric salts (e.g., acetate, borate, or nitrate), and combinations thereof.

In embodiments, the compositions herein include a co-solvent. For example, in some instances the solubility of gaboxadol may be well below the therapeutic dose and therefore a co-solvent system may be used. A co-solvent is a mixture of solvents that may be used to achieve sufficiently high solubility and may increase the stability. For example, co-solvents may be a water-miscible organic solvents, such as ethanol, propylene, glycol, Capmul PG, propylene glycol, glycerin, polyethylene glycol, sorbitol, dimethylacetamide, and/or dimethylsulfoxide (DMSO). In embodiments, the cosolvent may comprise up to about 75% of the pharmaceutical composition. In other embodiments the amount of cosolvent used include up to about, e.g., 1%, 5%, 10%, 15%, 25%, 40%, 50%, of the pharmaceutical composition.

The dosage forms may be prepared, for example, by mixing of an allosteric modulator and/or gaboxadol, or a pharmaceutically acceptable salt thereof, and one or more excipients (e.g., buffering agents, solubilizing agents, tonicity agents, antioxidants, chelating agents, antimicrobial agents and/or preservatives) in a blender under sterile conditions until a uniform blend is obtained. Pre-sterilized vials may then be filled with an appropriate amount of the sterile blend. The predetermined amount of sterile blend may then be mixed with a solvent, e.g., water, saline, about 5-10% sugar (e.g., glucose, dextrose) solution and combinations thereof prior to administration. In addition, the solution may be frozen and thawed prior to further processing.

The excipients may be used in solid or in solution form. When used in solid form, the excipients and an allosteric modulator and/or gaboxadol, or a pharmaceutically acceptable salt thereof, may be mixed together as described above, and then solvent added prior to parenteral administration. When used in solution form, the allosteric modulator and/or gaboxadol, or a pharmaceutically acceptable salt thereof, may be mixed with a solution of the excipient prior to parenteral administration.

Parenteral solutions including an allosteric modulator and/or gaboxadol, or a pharmaceutically acceptable salt thereof, may be prepared by mixing the required amount of allosteric modulator and/or gaboxadol, or a pharmaceutically acceptable salt thereof, which may be purified prior to use in parenteral fluids such as D5W, distilled water, saline or PEG and adjusting the pH of this solution between 6.8-8. The process may be carried out at room temperature, or to increase concentration, the solution may be warmed appropriately. Other solvents such as PEG 400, 600, polypropylene glycol or other glycols can be used to enhance solubility. The resulting solutions after cooling to room temperature, may be sterilized by known means such as ultrafiltration using, e.g., 0.45 micron filter or ethylene oxide treatment or heating and may be packaged into ampules, vials or pre-filled syringes suitable for dispensing a sterile parenteral formulation.

When administered, the parenteral compositions herein provide a time of maximum plasma concentration ($T_{max}$) for gaboxadol in human patients of about 1 or more hours (e.g., about 1.5 or more hours). In embodiments, a $T_{max}$ of gaboxadol in human patients ranging from between, e.g., about 1 to about 5 hours, about 1 to about 4 hours, about 1 to about 3 hours, about 1 to about 2 hours. In embodiments, a $T_{max}$ for gaboxadol in human patients of more than about 1.5 is observed. In embodiments, a $T_{max}$ for gaboxadol in human patients of less than about 3 hours is observed. The time of maximum plasma concentration is measured once infusion is complete.

In embodiments herein a dosage form includes from about 1 mg to about 500 mg gaboxadol, wherein parenteral administration (e.g., intramuscular, intravenous, subcutaneous, intraperitoneal, or intrathecal) of the dosage form provides an in vivo plasma profile for gaboxadol encompassing a mean $AUC_{0-\infty}$ of more than about 25 ng·hr/ml. In embodiments, single dose administration of the dosage form provides an in vivo plasma profile for gaboxadol encompassing a mean $AUC_{0-\infty}$ of more than about, e.g., 50 ng·hr/ml, 75 ng·hr/ml, 150 ng·hr/ml, 250 ng·hr/ml, 500 ng·hr/ml, 1000 ng□hr/ml, or 1500 ng□hr/ml.

In embodiments, the dosage form includes from about 1 mg to about 500 mg gaboxadol, wherein administration of the dosage form provides an in vivo plasma profile for gaboxadol encompassing a mean $C_{max}$ of less than about 10000 ng/ml. In embodiments, single dose administration of the compositions provide an in vivo plasma profile for gaboxadol of a mean $C_{max}$ of less than about, e.g., 5000 ng/ml, 2500 ng/ml, 1000 ng/ml, 500 ng/ml, 250 ng/ml, or 100 ng/ml.

In embodiments, pharmaceutical compositions for parenteral administration include gaboxadol or a pharmaceutically acceptable salt thereof wherein parenteral administration exhibits a pharmacokinetic profile of a $T_{max}$ at about 1 to about 120 minutes after administration of the parenteral composition; followed by a plasma drug concentration of at least 50% $C_{max}$ for a duration of about 90 to about 360 minutes. In embodiments, parenteral administration of gaboxadol is followed by a plasma drug concentration of at least 50% $C_{max}$ for a duration of, e.g., about 10 to about 60 minutes, about 15 to about 90 minutes, about 30 to about 120 minutes, about 60 to about 180 minutes, about 90 to about 180 minutes.

In embodiments, stable pharmaceutical compositions are provided in unit dosage form in a vial or ampoule suitable for parenteral administration having a therapeutically effective amount of allosteric modulator and/or gaboxadol, or a pharmaceutically acceptable salt thereof, dissolved in sterile water to form a solution wherein the composition is substantially free of any excipient, organic solvent, buffer, acid, base, salt other than allosteric modulator and/or gaboxadol, or a pharmaceutically acceptable salt thereof. In embodiments, the pharmaceutical composition remains sufficiently soluble and is capable of direct administration. In embodiments, the pharmaceutical composition is capable of storage in the absence of an inert atmosphere for at least 6 months.

In embodiments, provided herein are stable pharmaceutical compositions in unit dosage form in a vial or ampoule suitable for parenteral administration having a therapeutically effective amount of allosteric modulator and/or gaboxadol, or a pharmaceutically acceptable salt thereof, dissolved in sterile water to form a solution wherein the composition is free of any excipient, organic solvent, buffer, acid, base, salt other than allosteric modulator and/or gaboxadol, or a pharmaceutically acceptable salt thereof. In embodiments, the pharmaceutical composition remains sufficiently soluble and is capable of direct administration. In embodiments, the pharmaceutical composition is capable of storage in the absence of an inert atmosphere for at least 6 months.

In embodiments, stable pharmaceutical compositions suitable for parenteral administration include allosteric modulator and/or gaboxadol, or a pharmaceutically acceptable salt thereof, in an aqueous solution having an osmolarity between 225 and 350 mOsm/kg and at a pH in the range between 7.0 and 8.0. In embodiments, the aqueous solution has an osmolarity between 270 and 310. In embodiments, the aqueous solution has a pH in the range between 7.2 and 7.8.

In embodiments, provided herein are methods of treating an epileptic disorder including administering to a patient in need thereof a first pharmaceutical and a second pharmaceutical composition including gaboxadol or a pharmaceutically acceptable salt thereof, and/or an allosteric modulator, wherein the second pharmaceutical composition that provides a stable in vivo plasma profile having a mean $AUC_{0-\infty}$ of at least about, e.g., 25%, 30%, 35%, 40%, 45% or 50% less than the first pharmaceutical composition. In embodiments, the composition provides improvement of next day functioning of the patient. For example, the composition may provide improvement in one or more symptoms for more than about, e.g., 6 hours, 8 hours, 10 hours, or 12 hours after administration of the first and/or second pharmaceutical composition.

In embodiments, parenteral compositions may be administered as needed, e.g., once, twice, thrice or four or more times daily, or continuously depending on the patient's needs. In embodiments, the parenteral compositions may be administered immediately or as soon thereafter as seizures start. In embodiments, the parenteral compositions may be administered as soon as warning signs of a seizure are exhibited such as auras, unusual smells, usual feelings, etc.

In embodiments, provided herein are methods of treating an epileptic disorder including administering to a patient in need thereof a first pharmaceutical dosage including a sub-therapeutic dosage of an allosteric modulator wherein the composition provides improvement for more than 6 hours after administration.

In embodiments, provided herein are methods of treating an epileptic disorder including administering to a patient in need thereof a first pharmaceutical dosage including a sub therapeutic dosage of gaboxadol or a pharmaceutically acceptable salt thereof wherein the composition provides improvement for more than 6 hours after administration.

In embodiments, provided herein are methods of treating an epileptic disorder including administering to a patient in need thereof a first pharmaceutical composition including an allosteric modulator and a second pharmaceutical composition including gaboxadol or a pharmaceutically acceptable salt thereof wherein the second pharmaceutical composition provides an in vivo plasma profile having a mean $AUC_{0-\infty}$ of less than about 900 ng·hr/ml. In embodiments, the second pharmaceutical composition provides an in vivo plasma profile having a $AUC_{0-\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0-\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0-\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement of next day functioning of the patient. In embodiments, the first pharmaceutical composition provides improvement in one or more symptom for more than, e.g., 6 hours, 8 hours or 12 hours after administration of the first pharmaceutical composition.

In embodiments, provided herein are methods of treating an epileptic disorder including administering to a patient in need thereof a first pharmaceutical composition including an allosteric modulator and a second pharmaceutical composition including gaboxadol or a pharmaceutically acceptable salt thereof wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments, the $T_{max}$ of the first pharmaceutical composition is less than 3 hours. In embodiments, the $T_{max}$ of the first pharmaceutical composition is less than 2.5 hours. In embodiments, the $T_{max}$ of the first pharmaceutical composition is less than 2 hours. In embodiments, the $T_{max}$ of the first pharmaceutical composition is less than 1.5 hours. In embodiments, the $T_{max}$ of the first pharmaceutical composition is less than 1 hour.

In embodiments, the first pharmaceutical composition provides a dissolution of at least about 80% within the first 20 minutes of administration to a patient in need thereof. In embodiments, the first pharmaceutical composition provides a dissolution of at least about, e.g., 85%, 90% or 95% within the first 20 minutes of administration to a patient in need thereof. In embodiments, the first pharmaceutical composition provides a dissolution of at least 80% within the first 10 minutes of administration to a patient in need thereof.

In embodiments the first and/or the second pharmaceutical compositions are sub therapeutic dosages. A sub therapeutic dosage is an amount of active substance, e.g., allosteric modulator and/or gaboxadol, or a pharmaceutically acceptable salt thereof, that is less than the amount required for a therapeutic effect. In embodiments, a sub therapeutic dosage is an amount of allosteric modulator or a pharmaceutically acceptable salt thereof that alone may not provide improvement in at least one symptom of the epileptic disorder but is sufficient to maintain such improvement. In embodiments, a sub therapeutic dosage is an amount of gaboxadol pharmaceutically acceptable salt thereof that alone may not provide improvement in at least one symptom of the epileptic disorder but is sufficient to maintain such improvement. In embodiments, the methods provide administering a first pharmaceutical composition that provides improvement in at least one symptom of an epileptic disorder and a second composition that maintains the improvement. In embodiments, after administration of the first pharmaceutical composition, the second pharmaceutical composition may provide a synergistic effect to improve at least one symptom of an epileptic disorder. In embodiments the second pharmaceutical composition may provide a synergistic effect to improve at least one symptom of an epileptic disorder.

In embodiments, provided herein are methods of treating an epileptic disorder including administering to a patient in need thereof a pharmaceutical composition including a first pharmaceutical dosage wherein the composition provides improvement for more than 6 hours after administration and a second pharmaceutical composition including a sub therapeutic dosage of gaboxadol or a pharmaceutically acceptable salt thereof.

Administration of the first and second pharmaceutical compositions may be simultaneous or separated by an interval of time to achieve immediate, intermediate or long-term improvement in at least one symptom. In embodiments, the first and second pharmaceutical composition may be administered 6 hours apart. In embodiments, the first and second pharmaceutical composition may be administered 12 hours apart. In embodiments, the first and second pharmaceutical compositions may administered within, e.g., 15 minutes, 30 minutes, 1 hour, 2 hours, 6 hours, 12 hours, 18 hours, 24 hours etc. In embodiments, the first and second pharmaceutical composition may be administered ogether. In embodiments, the first and second pharmaceutical compositions may administered separated by at least, e.g., 15 minutes, 30 minutes, 1 hour, 2 hours, 12 hours, 18 hours, 24 hours etc. In embodiments, improvement in at least one symptom of an epileptic disorder for more than 8 hours after administration to the patient is provided. In embodiments, improvement for more than about, e.g., 10 hours, 12 hours, 15 hours, 18 hours, 20 hours, or 24 hours after administration to the patient is provided.

In embodiments, the administration of the first and second pharmaceutical composition may provide a synergistic effect to improve at least one symptom of an epileptic disorder.

In embodiments, the first and/or the second pharmaceutical composition include any of the aforementioned amounts of active substance, e.g., allosteric modulator and/or gaboxadol a pharmaceutically acceptable salt thereof.

In embodiments, the first and/or the second pharmaceutical composition include 5 mg to 15 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg active substance, e.g., allosteric modulator and/or gaboxadol.

In embodiments, the first and/or the second pharmaceutical composition include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg active substance, e.g., allosteric modulator and/or gaboxadol or amounts that are multiples of such doses. In embodiments, the first pharmaceutical compositions include 2.5 mg, 5 mg, 7.5 mg, 10 mg, 15 mg, or 20 mg of an allosteric modulator. In embodiments, the second pharmaceutical compositions include 2.5 mg, 5 mg, 7.5 mg, 10 mg, 15 mg, or 20 mg of an allosteric modulator.

In embodiments, methods of treating epileptic disorders include administration of an allosteric modulator and/or gaboxadol or a pharmaceutically acceptable salt thereof, in combination with one or more other active compounds. The combination therapies can include administration of the active agents together in the same admixture, or in separate admixtures. In embodiments, the pharmaceutical composition includes two, three, or more active agents. In embodiments, the combinations result in a more than additive effect on the treatment of the disease or disorder. Thus, treatment is provided of an epileptic disorder with a combination of agents that combined, may provide a synergistic effect that enhances efficacy.

In embodiments, gaboxadol or a pharmaceutically acceptable salt thereof, is administered in combination with conventional therapy for seizures, epilepsy, or one of the other disorders disclosed herein. For example, common conventional therapies for seizures and epilepsy include antiepileptic drugs and non-antiepileptic drug treatments such as low carbohydrate diet (e.g., ketogenic diets, such as classical diet, medium chain triglyceride (MCT) diet, modified Atkins diet (MAD), and low glycemic index treatment (LGIT)), intravenous immunoglobulin, steroids, elimination diet, valgus nerve stimulation, corticetomy, and multiple subpial transections.

Common antiepileptic and anticonvulsive active compounds that may be used in combination with an allosteric modulator and/or gaboxadol or a pharmaceutically acceptable salt thereof include, but are not limited to, acetazolamide, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

The disclosed compounds, such as gaboxadol or pharmaceutically acceptable salts thereof, or an allosteric modulator, pharmaceutically acceptable salts, derivatives and/or analogues thereof, can be used individually as a monotherapy as the only active agent. In embodiments, methods are provided of treating epileptic disorders using an allosteric modulator or a pharmaceutically acceptable salt thereof. In embodiments, methods of treating epileptic disorders include administration of an allosteric modulator, pharmaceutically acceptable salts, derivatives and/or analogues thereof in combination with one or more other active agent, e.g., allosteric modulator or gaboxadol. The combination therapies can include administration of the active agent, e.g., allosteric modulator or gaboxadol, together in the same admixture, or in separate admixtures. In embodiments, the pharmaceutical composition includes two, three, or more active agents. In embodiments, the combinations result in a more than additive effect on the treatment of the disease or disorder. Thus, treatment is provided of an epileptic disorder with a combination of agents that combined, may provide a synergistic effect that enhances efficacy.

In embodiments, gaboxadol or pharmaceutically acceptable salts thereof, or an allosteric modulator, pharmaceutically acceptable salts, derivatives and/or analogues thereof, or both, is administered in combination with conventional therapy for seizures, epilepsy, or one of the other disorders disclosed herein. For example, common conventional therapies for seizures and epilepsy include antiepileptic drugs and non-antiepileptic drug treatments such as low carbohydrate diet (e.g., ketogenic diets, such as classical diet, medium chain triglyceride (MCT) diet, modified Atkins diet (MAD), and low glycemic index treatment (LGIT)), intravenous immunoglobulin, steroids, elimination diet, valgus nerve stimulation, corticetomy, and multiple subpial transections.

Common antiepileptic and anticonvulsive active compounds that may be used in combination with an allosteric modulator include, but are not limited to, acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

In embodiments, a co-therapy of an allosteric modulator, a pharmaceutically acceptable salt thereof, or a derivative thereof and gaboxadol or a pharmaceutically acceptable salt thereof is effective to reduce seizure frequency or severity in the subject greater than either compound is administered alone. In embodiments, the co-therapy produces a more than additive result compared to compounds administered individually.

In embodiments, the subject may be started at a low dose and the dosage is escalated. In this manner, it can be determined if the drug is well tolerated in the subject. Dosages can be lower for children than for adults.

In embodiments, such as combination therapies, a dose of gaboxadol for children can be 0.1 mg/kg to 1 mg/kg, and the dose for an allosteric modulator may be 0.01 mg/kg to 0.1 mg/kg. In embodiments, the weight/weight ratio of gaboxadol and an allosteric modulator can be 10-to-1. However, the dosing ratio based on milligrams of active pharmaceutical ingredient (API) can range from 0.1-to-1 to 100-to-1 of gaboxadol-to-an allosteric modulator respectively.

Effective treatment of an epileptic disorder (e.g., acute repetitive seizure) herein may be established by showing reduction in the frequency of seizures (e.g., more than 50%) after a period of time compared with baseline. For example, after a baseline period of 1 month, the patients may be randomly allocated gaboxadol or an allosteric modulator or placebo as add-on therapy to standard therapies, such as valproate and clobazam, during a double-blind period of 2 months. Primary outcome measurements may include the percentage of responders on gaboxadol or an allosteric modulator and on placebo, defined as having experienced at least a 50% reduction of clonic (or tonic-clonic) seizure frequency during the second month of the double-blind period compared with baseline. Patients who present with status epilepticus during the double-blind period may be regarded as non-responders. Secondary outcomes may include the absolute count of clonic (or tonic-clonic) seizures during the second month of the double-blind period (normalized to 30 days, by dividing the raw count by the exact number of days of observation and multiplying by 30) and the percentage of change from baseline.

The effectiveness of gaboxadol and/or an allosteric modulator for the treatment of a disclosed epileptic disorder, e.g., associated with Dravet syndrome or Lennox-Gastaut syndrome, may be established in other controlled studies. For example, a randomized, double-blind, placebo-controlled study consisting of a 4-week baseline period followed by a 3-week titration period and 12-week maintenance period may be used in patients age 2-54 years with a current or prior diagnosis of Dravet syndrome or LGS. Multiple target maintenance doses of gaboxadol and/or an allosteric modulator may be tested according to patient body weight and specific dosing regime. A primary efficacy measure may include the percent reduction in the weekly frequency of drop seizures (atonic, tonic, or myoclonic), also known as drop attacks, from the 4-week baseline period to 12-week maintenance period. Thus, efficacy may be measured as percentage reduction in weekly seizure (e.g., atonic, tonic, or myoclonic) frequency from baseline of, e.g., 0 to <20, 20 to <40, 40 to <60, 60 to <80, 80 to <100.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "treating" or "treatment" refers to alleviating, attenuating or delaying the appearance of clinical symptoms of a disease or condition in a subject that may be afflicted with or predisposed to the disease or condition, but does not yet experience or display clinical or subclinical symptoms of the disease or condition. In certain embodiments, treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" may also refer to inhibiting the disease or condition, e.g., arresting or reducing its epileptic or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic treatment are two separate embodiments of the disclosure herein.

"Effective amount" or "therapeutically effective amount" means a dosage sufficient to alleviate one or more symptom of a disorder, disease, or condition being treated, or to otherwise provide a desired pharmacological and/or physiologic effect.

"Improvement" refers to the treatment of symptoms or conditions associated with epileptic disorders, measured relative to at least one symptom or condition of the metabolic disease.

"Improvement in next day functioning" or "wherein there is improvement in next day functioning" refers to improvement after waking from an overnight sleep period wherein the beneficial effect of administration of one or more of gaboxadol or a pharmaceutically acceptable salt thereof alone, or an allosteric modulator alone, or gaboxadol in combination an allosteric modulator, applies to at least one symptom or condition associated with an epileptic disorder and is discernable, either subjectively by a patient or objectively by an observer, for a period of time, e.g., immediately, 1 hour, 2 hours, hours, 3 hours, 4 hours, 5 hours, 6 hours, 12 hours, 24 hours, etc. after waking.

"Composition", "pharmaceutical composition", "formulation", "pharmaceutical formulation" are used interchangeably herein. "Composition", "pharmaceutical composition", "formulation", "pharmaceutical formulation" encompass dosage forms. Dosage forms can encompass unit doses.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

As used herein, the term "prevention" or "preventing" means to administer a composition to a subject or a system at risk for or having a predisposition for one or more symptoms caused by a disease or disorder to facilitate cessation of a particular symptom of the disease or disorder, a reduction or prevention of one or more symptoms of the disease or disorder, a reduction in the severity of the disease or disorder, the complete ablation of the disease or disorder, stabilization or delay of the epileptic or progression of the disease or disorder.

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity.

"Analog" "analogue, and "derivative" are used herein interchangeably and refer to a compound that possesses the same core as the parent compound, but may differ from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diasteromers can be resolved or separated using techniques known in the art. "Chirality" also includes axial and planar chirality.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts. The pharmaceutically acceptable salts of the compounds can be synthesized from the parent compound, which contains a basic or acidic moiety, by conventional chemical methods. For example, gaboxadol may be formulated for administration to a patient using pharmaceutically acceptable salts including acid addition salts, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

"Excipient" is a substance, other than the active drug substance, e.g., gaboxadol, of a pharmaceutical composition, which has been appropriately evaluated for safety and are included in a drug delivery system to either aid the processing of the drug delivery system during its manufacture; protect; support; enhance stability, bioavailability, or patient acceptability; assist in product identification; or enhance any other attributes of the overall safety and effectiveness of the drug delivery system during storage or use.

"Stabilizer" or "stabilizing amount" refers to an amount of one or more excipients included in the parenteral compositions that provide sufficient stability but do not adversely affect the bioavailability, safety and/or efficacy of allosteric modulator and/or gaboxadol or pharmaceutically acceptable salt thereof used in the composition.

"Stable" means that there is substantially no degradation of the gaboxadol or pharmaceutically acceptable salt thereof after a specified period of time, e.g., after 3 months or 6 months.

"Soluble" means that the solution of allosteric modulator and/or gaboxadol or pharmaceutically acceptable salt thereof does not turn hazy and/or there is substantially no precipitate in the solution "Sufficiently soluble" means that the particle content is sufficiently low, and the material is sufficiently sterile such that it is useful for parenteral administration. For example, the number of particles in a liquid composition should be, e.g., less than 6,000 10 µm particles should be present in a volume of 10 ml solvent, preferably less than 10,000, less than 5,000, less than 3,000, less than 1,000, or less than 400 10 µm particles. In some examples, the number of particles in a liquid composition should be less than 1000, less than 600, or less than 200 25 µm particles in the 10 ml volume.

"Local site compatible" herein shall mean the composition is tolerant at the site of injection or infusion, thus minimizing side effects, such as local skin irritations or venous irritations, including inflammatory reactions at the infusion site. The parenteral compositions herein may have less side reactions than conventional products, such as skin irritation or phlebitis.

"Purified" as used herein refers to material that has been isolated under conditions that reduce or eliminate the presence of unrelated materials, i.e., contaminants, including native materials from which the material is obtained. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated, for example, by chromatography or any other methods known in the art. In embodiments, purified means that the level of contaminants is below a level acceptable to regulatory authorities for safe administration to a human or non-human animal.

"Ready-to-use" with reference to the compositions herein shall mean the preparation in the reconstituted form, with standardized concentration and quality, prefilled in the single-use container, such as glass vials, infusion bags or syringes, ready for direct administration to the patient.

"Direct administration" with reference to the compositions herein shall mean the immediate administration, i.e., without further dilution, premixing with other substances or otherwise changing the composition or formulation of the composition. Such composition is typically directly discharged from an infusion device and administered via a vascular access port or through a central line.

"Dosage" is intended to encompass a formulation expressed in terms of µg/kg/day, µg/kg/hr, mg/kg/day or mg/kg/hr. The dosage is the amount of an ingredient administered in accordance with a particular dosage regimen. A "dose" is an amount of an agent administered to a mammal in a unit volume or mass, e.g., an absolute unit dose expressed in mg or µg of the agent. The dose depends on the concentration of the agent in the formulation, e.g., in moles per liter (M), mass per volume (m/v), or mass per mass (m/m). The two terms are closely related, as a particular dosage results from the regimen of administration of a dose or doses of the formulation. The particular meaning in any case will be apparent from context.

"Patient" and "subject" are used interchangeably herein and include, but not limited to, primates such as humans, canines, porcine, ungulates, rodents, poultry, and avian.

"Co-administered with", "in combination with", "administered in combination with", "a combination of", "administered along with", or "co-therapy", may be used interchangeably and mean that two or more agents are administered in the course of therapy. The agents may be administered together at the same time or separately in spaced apart intervals. The agents may be administered in a single dosage form or in separate dosage forms.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml or µg·hr/ml). The area under the curve is governed by clearance. Clearance is defined as the volume of blood or plasma that is totally cleared of its content of drug per unit time (ml/min).

EXAMPLES

The Examples provided herein are included solely for augmenting the disclosure herein and should not be considered to be limiting in any respect.

Example 1

Gaboxadol Plasma Concentration Profiles

The following Example provides the plasma concentration profiles and dose proportionality of gaboxadol monohydrate following single oral doses ranging from 2.5 to 20 mg. The absolute bioavailability of gaboxadol monohydrate capsules ranging from 2.5 to 20 mg is also assessed.

This study was composed of separate groups of 10 healthy adult subjects (at least 4 of each gender) who participated in a 6-period, double-blind, randomized, crossover study designed to access the dose proportionality and absolute bioavailabilty of 5 single oral doses of gaboxadol across the dose range of 2.5 to 20 mg. The order in which the subjects received the 5 single oral doses of gaboxadol (2.5; 5; 10; 15; and 20 mg) was randomized within Treatment Periods 1 through 5. Each subject was expected to complete all 6 treatment periods and there was a washout of at least 4 days between each treatment period.

Each oral dosing within Treatment Periods consisted of 2 capsules of test drug taken simultaneously at each scheduled dosing. The treatment designations for the orally administered study drugs were as follows: Treatment A—one 2.5 mg gaboxadol capsule and 1 matching placebo capsule; Treatment B—one 5 mg gaboxadol capsule and 1 matching placebo capsule; Treatment C—one 10 mg gaboxadol capsule and 1 matching placebo capsule; Treatment D—one 15 mg gaboxadol capsule and 1 matching placebo capsule; and Treatment E—20 mg gaboxadol (two 10 mg gaboxadol capsules). Subjects received their study drug after an overnight fast with 240 mL of water in the morning about 8:00 AM. Water was permitted ad libitum except within 1 hour prior to and after study drug administration. No food was allowed for 4 hours post dose.

For each subject in each treatment, plasma and urine samples were collected over 16 hours post-dosing for the determination of pharmacokinetic parameters (e.g., AUC, $C_{max}$, $T_{max}$, apparent $t_{1/2}$, cumulative urinary excretion, renal clearance, clearance, and steady-state volume of distribution, as appropriate). AUC and $C_{max}$ for gaboxadol were potency adjusted to facilitate comparison of pharmacokinetic data across studies. Table 1 provides the individual potency-adjusted pharmacokinetic parameters of gaboxadol following single oral doses (2.5, 5, 10, 15, and 20 mg).

TABLE 1

Pharmacokinetic parameters for gaboxadol following oral and IV administration

| Parameter | Geometric Mean (N = 10) | | | | | | Slope (90% CI)[††] |
|---|---|---|---|---|---|---|---|
| | 2.5 mg | 5 mg | 10 mg Oral | 10 mg I.V. | 15 mg | 20 mg | |
| $AUC_{0-\infty}$ (ng·hr/mL) | 90 | 171 | 346 | 380 | 539 | 669 | 0.98 (0.95, 1.01) |
| $C_{max}$ (ng/mL)[†] | 61 | 110 | 232 | 212 | 382 | 393 | 0.95 (0.88, 1.02) |
| $T_{max}$ (hr)[‡] | 0.5 | 0.6 | 0.5 | — | 0.5 | 0.6 | |
| Apparent $t_{1/2}$ (hr)[§] | 1.5 | 1.5 | 1.6 | 1.5 | 1.5 | 1.6 | |
| CL/F (mL/min)[ᵃ] | 461 | 488 | 476 | 438 | 469 | 499 | |
| $F_e$ (%) | 43 | 45 | 53 | 53 | 50 | 53 | |
| $CL_R$ (mL/min) | 196 | 222 | 250 | 208 | 234 | 265 | |
| F (%) (90% CI)[#] | | | 92% (0.86, 0.97) | | | | |

[†]$C_{\infty i}$ (ng/mL) for 10 mg. IV.
[‡]Median.
[§]Harmonic Mean.
[ᵃ]CL (mL/min) for 10 mg IV.
[#]Bioavailability relative to 10 mg I.V. reference based on pooled dose-adjusted (to 10 mg) oral $AUC_{0-\infty}$ values.
[††]Dose proportionality assessment of oral treatments only.

Example 2

Assessment of Residual Effects Resulting from Gaboxadol Administration

This study was a double blind, double-dummy, randomized, active- and placebo-controlled, single dose, 3-period crossover study, followed by an open-label, single-dose, single period study in healthy elderly male and female subjects. Subjects were randomized to each of 3 treatments (Treatments A, B, and C) to be administered in a crossover manner over the first 3 treatment periods. For Treatment A, subjects received a single dose of gaboxadol 10 mg; for Treatment B, subjects received a single dose of flurazepam 30 mg; and for Treatment C, subjects received a single dose of placebo. Doses were administered orally at bedtime on Day 1. Subjects were domiciled from early in the evening of dosing until ~36 hours post-dose (morning of Day 3) during each treatment period. The subjects who participated in treatment periods 1-3 participated in a fourth treatment period. In this period, a single dose of gaboxadol 10 mg (Treatment D) was administered orally in an open-label manner on the morning of Day 1 for PK of gaboxadol. There was at least a 14-day washout between the doses of consecutive treatment periods. Study participants included healthy, elderly male and female subjects between 65 and 80 years of age, with a Mini Mental Status 24, weighing at least 55 kg. All subjects received 10 mg gaboxadol monohydrate capsules and 30 mg flurazepam (provided as 2×15 mg capsules), matching placebo was provided for both gaboxadol and flurazepam.

The primary endpoints evaluated included pharmacodynamics (measurement of psychomotor performance, memory, attention and daytime sleepiness the following pm dosing), gaboxadol pharmacokinetics, and safety. Gaboxadol (single dose 10 mg) did not show residual effect 9 hours post-dose on the primary endpoints Choice Reaction Time and Critical Flicker Fusion, whereas the active reference Flurazepam (30 mg single dose) showed significant effect on the same tests. In addition, gaboxadol did not show any signs of residual effects on other measurements applied in the study (Multiple Sleep Latency Test (MSLT); Digit symbol substitution test (DSST), Tracking, Memory tests, Body Sway, and Leeds Sleep Evaluation Questionnaire).

Example 3

Evaluation of the Ability of Allopregnanolone, Ganaxolone, and Gaboxadol to Block Benzodiazepine-Resistant Status Epilepticus Allopregnanolone, ganaxolone, and gaboxadol are evaluated for acute anticonvulsant efficacy when administered with escalating doses at 30 min after the onset of convulsive status epilepticus, a time-point typically resistant to benzodiazepines. Results obtained with these agents are compared to those obtained from side-by-side studies with vehicle-treated animals.

Twenty-four hours prior to administration of the chemoconvulsant pilocarpine, male Sprague Dawley rats (n=10 time or treatment/group, 100-125 g; Charles River Laboratories) are treated systemically with lithium chloride (127 mg/kg; (intraperitoneal (i.p.)). On the next day, the rats receive pilocarpine hydrochloride (50 mg/kg; i.p.) and are monitored carefully for the presence or absence of convulsive seizure activity. Administration of pilocarpine induces behavioral seizures within 5-20 min and any rat not showing convulsive seizure activity within 45 min of pilocarpine administration is excluded from further study. On the study day, the ability of each of the investigational compounds (allopregnanolone (ALLO), ganaxolone (GNX), or gaboxadol (GBD)) or vehicle (VEH) (40% hydroxypropyl β-cyclodextrin) to halt convulsive status epilepticus in the Li-Pilo model of status epilepticus is evaluated with escalating doses administered i.p. 30 min after the first observed convulsive seizure. Throughout the study, the experimenter conducting the behavioral observations is blinded to treatment conditions (i.e., allopregnanolone, ganaxolone, or gaboxadol). All rats are observed and scored for seizure severity for 120 min post drug administration, and any accompanying behavioral effects are also noted by an experimenter blinded to treatment conditions. At the conclusion of the behavioral observation period, a 3 mL injection of lactated Ringer's solution is administered to all surviving rats to replace any SE-induced fluid loss.

The dose of each of the investigational compounds (allopregnanolone, ganaxolone, or gaboxadol) is varied in groups of ten rats until at least two points are established between the limits of 100% protection (no further convulsive seizures after 10 min of drug administration) and 0% protection. The dose of drug required to produce the desired endpoint in 50% of animals (ED50 or TD50) and the 95% confidence interval is calculated by a computer program based on the Probit method (Finney D J. Probit Analysis. Cambridge University Press. 1971). This dose response evaluation typically requires up to 5 treatment groups per investigational compound, for a total of up to 50 rats per compound. Thus, up to 150 rats can be used for the investigational compounds (allopregnanolone, ganaxolone, or gaboxadol) quantification, and there is also one vehicle treatment group (n=10), such that the total number of rodents in Study 1 is 160. All animals in the study are retained for 24 hours following completion of the study for assessment of weight change. The doses administered for allopregnanolone, ganaxolone, or gaboxadol are 0.5 mg/kg, 2 mg/kg, 5 mg/kg, 10 mg/kg, or 20 mg/kg.

Figure 2:
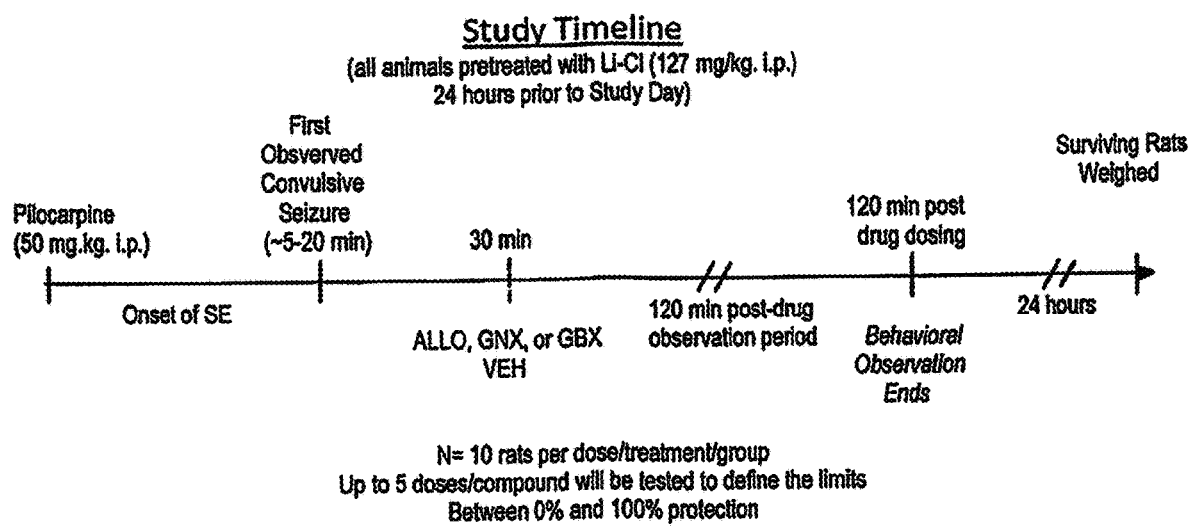
FIG. 2 is a schematic drawing depicting a timeline for an evaluation study of the ability of allopregnanolone, ganaxolone and gaboxadol to block benzodiazepine resistant status epilepticus in rats.

Pharmacokinetics Sample Collection: Brains and plasma may be collected for assessment from a satellite cohort of rats for each dose (n=3 rats/dose/compound; up to 45 rats in total). Plasma is collected from trunk blood after 10,000×g centrifugation for 10 min at 4° C. The anticoagulant is lithiumheparin. Brains are snap frozen on dry ice. All samples are stored at −20° C. The testing procedure timeline is set forth in FIG. 2.

Dose-response curves are constructed and expressed as ED50 (95% confidence intervals) calculated for each investigational compound (allopregnanolone, ganaxolone, or gaboxadol) administered 30 min after the first observed convulsive seizure. In cases that the data does not permit the calculation of an ED50 (95% confidence interval) because of lack of efficacy, the highest dose tested is noted. Additional measures of effects, e.g., motor impairment, weight change post-SE, or survival from SE for 24 hrs are also recorded during the studies for all treatment conditions.

TABLE 2

Overall survival and protection results

| Compound (dose, mg/kg) | Protection (includes PK rats) | 24-hour Survival (excludes PK rats) |
| --- | --- | --- |
| VEH (40% HPBCD) | 0/13 (0%) | 8/11# (72%) |
| ALLO (0.5 mg/kg) | 0/13 (0%) | 6/10 (60%) |
| GBD (0.5 mg/kg) | 2/13 (15%) | 7/10 (70%) |
| GNX (0.5 mg/kg) | 0/13 (0%) | 6/10 (60%) |
| ALLO (2 mg/kg) | 0/13 (0%) | 7/10 (70%) |
| GBD (2 mg/kg) | 0/13 (0%) | 8/10 (80%) |
| GNX (2 mg/kg) | 0/13 (0%) | 8/10 (80%) |
| ALLO (5 mg/kg) | 0/13 (0%) | 7/9 (72%) |
| GBD (5 mg/kg) | 0/13 (0%) | 6/11# (55%) |
| GNX (5 mg/kg) | 0/13 (0%) | 7/10 (70%) |
| ALLO (10 mg/kg) | 2/13 (15%) | 9/10 (90%) |
| GBD (10 mg/kg) | 0/13 (0%) | 10/10 (100%)* |
| GNX (10 mg/kg) | 1/13 (7.7%) | 9/10 (90%) |
| ALLO (20 mg/kg) | 1/13 (7.7%) | 9/10 (90%) |
| GBD (20 mg/kg) | 0/13 (0%) | 7/9 (78%) |
| GNX (20 mg/kg) | 4/13 (30.8%)* | 9/10 (90%) |

*Significantly different from VEH, p < 0.05
Spontaneous death during SE in PK group rat 110 min post -SE onset, but sample was collected.

Figure 3:
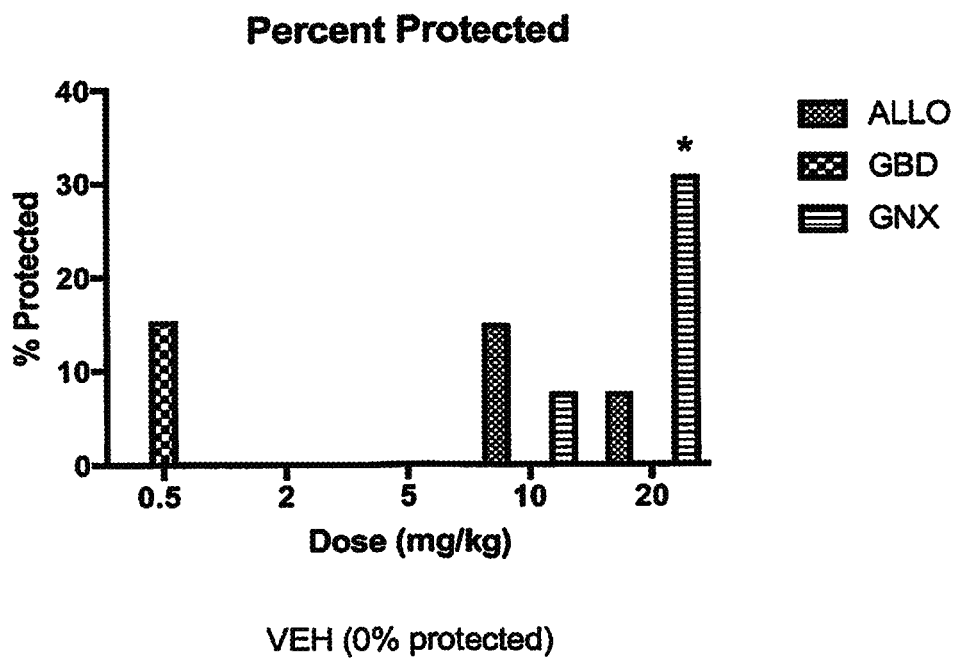
FIG. 3 is a bar graph depicting the percent protected versus dose with respect to allopregnanolone, ganaxolone, or gaboxadol.
Figure 4:
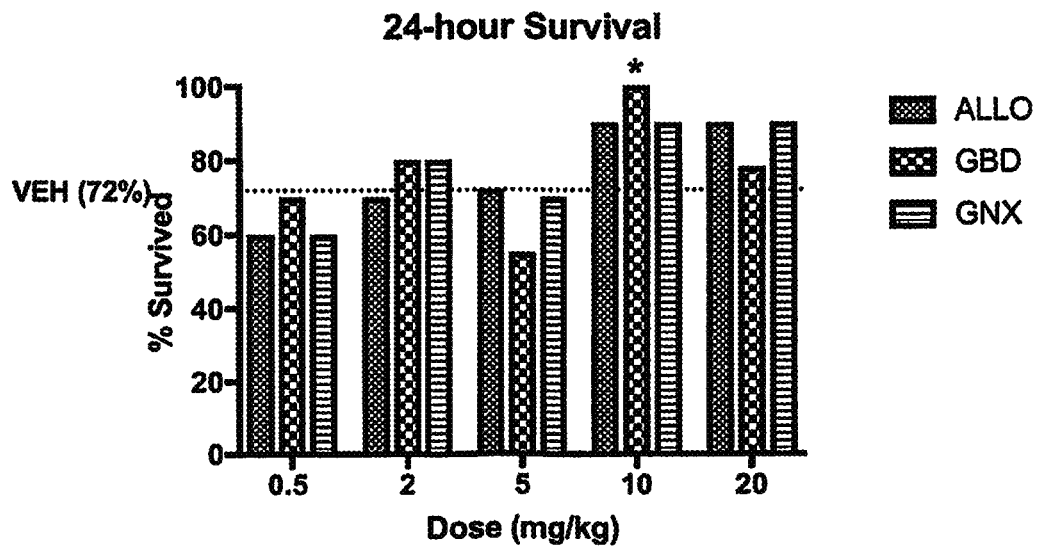
FIG. 4 is a bar graph depicting the 24-hour survival results based on dose with respect to allopregnanolone, ganaxolone, or gaboxadol.
Figure 5:
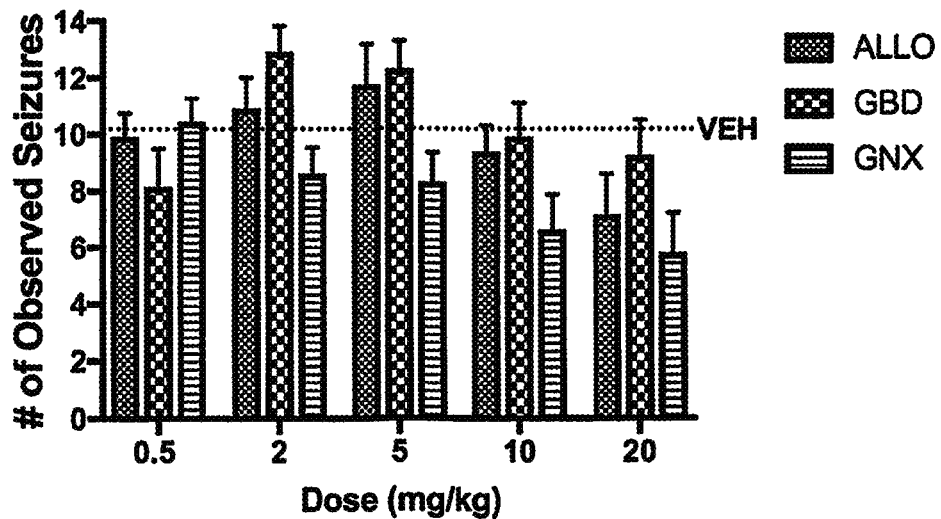
FIG. 5 is a bar graph showing the number of observed seizures versus dose of allopregnanolone, ganaxolone, or gaboxadol.
Figure 6A:
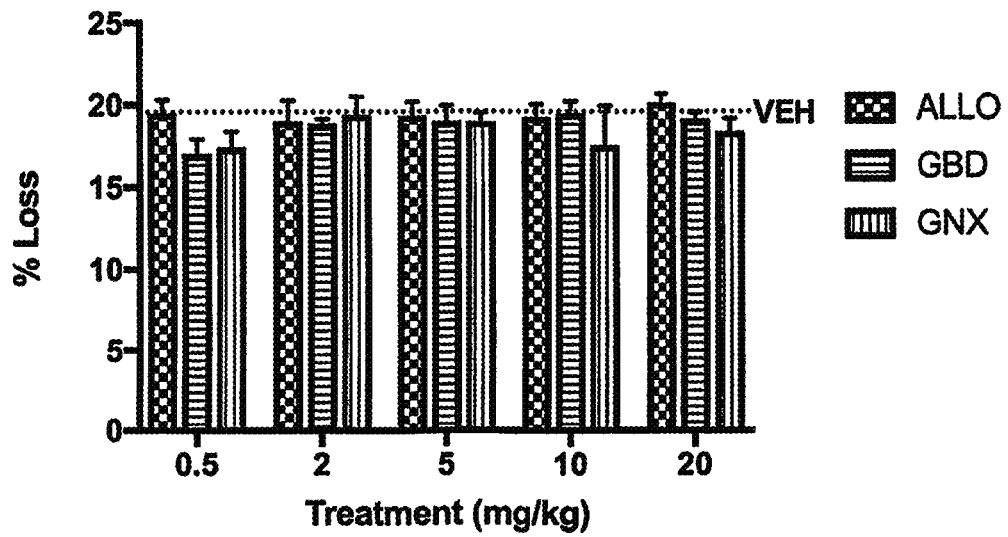
FIG. 6A is a bar graph showing body weight changes 24 hours post-status epilepticus as a function of percent loss versus dose.
Figure 6B:
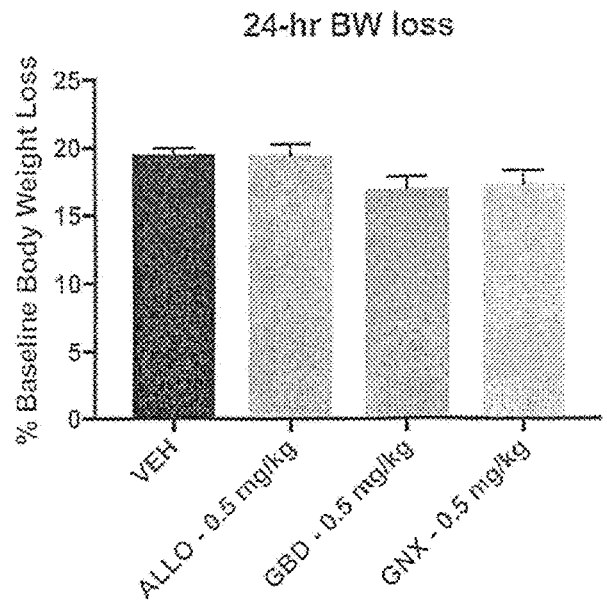
FIG. 6B is a bar graph showing 24 hour body weight loss for 0.5 mg/kg dose groups.

FIG. 3 is a bar graph showing the percent protected versus dose with respect to allopregnanolone, ganaxolone, or gaboxadol. FIG. 4 is a bar graph showing the 24-hour survival results based on dose with respect to allopregnanolone, ganaxolone, or gaboxadol. FIG. 5 is a bar graph showing the number of observed seizures versus dose. FIG. 6A is a bar graph showing body weight changes 24 hours post-status epilepticus as a function of percent loss versus dose. FIG. 6B is a bar graph showing 24 hour body weight loss for 0.5 mg/kg dose groups. Dose-response evaluation of treatment during benzodiazepine-resistant status epilepticus suggests dose-dependent efficacy of ganaxolone (i.p.)–significant (p<0.02) improvement in protection at 20 mg/kg. Potential for inverted U-response profile of gaboxadol (i.p.)–p=0.071 at 0.5 mg/kg. Significant improvements in 24-hour survival are shown for gaboxadol-treated rats (10 mg/kg).

Example 4

Prospective Study for the Characterization of the Ability of Allopregnanolone, Ganaxolone, and Gaboxadol to Block Benzodiazepine-Resistant Status Epilepticus Initial dose-response studies with intraperitoneal (i.p.) administration of allopregnanolone (ALLO), ganaxolone (GNX), and gaboxadol (GBD) suggests the potential for efficacy against benzodiazepine-resistant status epilepticus (Example 3). This study will assess the potential for synergistic activity of gaboxadol with either allopregnanolone, ganaxolone, or the benzodiazepine, lorazepam (LZP), against benzodiazepine-resistant status epilepticus in the Li-Pilo model in rats. Specifically, gaboxadol at low-doses (e.g. 0.5 mg/kg) will be administered in combination with a fixed dose of either allopregnanolone, ganaxolone, or lorazepam. The doses of allopregnanolone and ganaxolone will be those that were previously found to confer anticonvulsant effect in Example 3 (Table 2). The dose of lorazepam will be 2 mg/kg (Walton and Treiman. 1990. *Neurology* 40: 990-994 1990). The activity of each compound will also be evaluated alone. A vehicle-treatment group will be included. At 30 min post-status epilepticus onset, a single i.p. dose of each dose or dose combination (Table 3) will be administered to rats (n=13/group). Rats will be observed for presence or absence of further convulsive activity.

TABLE 3

Investigational Compounds and Combinations to be Evaluated (n = 13/rats treatment group with n = 3 rats sacrificed for PK analysis).

| Compound | Dose (all i.p.) |
| --- | --- |
| GBD | 0.25 mg/kg |
| GBD | 0.5 mg/kg |
| ALLO | 10 mg/kg |
| GNX | 20 mg/kg |
| GNX | 30 mg/kg |
| LZP | 2 mg/kg |
| GBD + ALLO | 0.5 mg/kg + 10 mg/kg |
| GBD + GNX | 0.5 mg/kg + 20 mg/kg |
| GBD + LZP | 0.5 mg/kg + 2 mg/kg |
| VEH | 40% HPβCD |

Twenty-four hours prior to administration of the chemoconvulsant pilocarpine, male Sprague Dawley rats (n=13 time or treatment/group; 100-125 g at arrival from Charles River Laboratories) will be treated systemically with lithium chloride (127 mg/kg; i.p.). On the next day, the rats will receive pilocarpine hydrochloride (50 mg/kg; i.p.) and monitored carefully for the presence or absence of convulsive seizure activity. Administration of pilocarpine induces behavioral seizures within 5-20 min and any rat not showing convulsive seizure activity within 45 min of pilocarpine administration will be excluded from further study. On the study day, the ability of each of the investigational compounds (allopregnanolone, ganaxolone, or gaboxadol) or vehicle (VEH) to halt convulsive status epilepticus in the Li-Pilo model of status epilepticus will be evaluated as outlined in Table 3 with administration 30 min after the first observed convulsive seizure. Throughout the study, the experimenter conducting the behavioral observations will be blinded to treatment conditions (e.g., allopregnanolone, ganaxolone, or gaboxadol, lorazepam, or VEH). All rats will be observed and scored for seizure severity for 120 min post drug administration, and any accompanying behavioral effects will also be noted by an experimenter blinded to treatment conditions. At the conclusion of the behavioral observation period, a 3 mL injection of lactated Ringer's solution will be administered to all surviving rats to replace any status epilepticus-induced fluid loss.

The dose of each of the investigational compounds will be administered to rats (n=13/compound dose; Table 3), for a total of 130 rats. A 15% non-responder rate is anticipated for rats pre-treated with Li—Cl, but that do not develop convulsive status epilepticus in the 45-minute time period. Thus, up to 150 rats will be used for this study, which includes potential non-responders. All animals in the study will be retained for 24 hours following completion of the study for assessment of weight change, as well as overall behavioral appearance at that time (e.g. lethargic/active). Behavioral appearance will be assessed by an investigator blinded to treatment condition.

Figure 7:
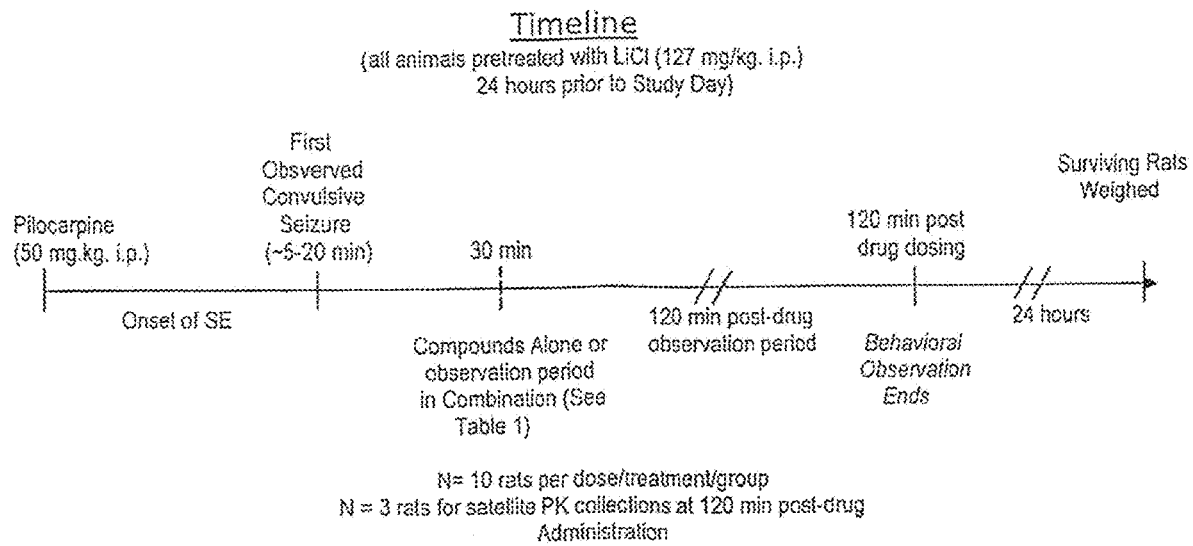
FIG. 7 is a schematic drawing depicting a timeline for a prospective evaluation study of the ability of allopregnanolone, ganaxolone and gaboxadol to synergistically block benzodiazepine resistant status epilepticus in rats.

Pharmacokinetics Sample Collection: Brains and plasma will be collected for assessment from a cohort of rats for each dose (n=3 rats/dose/compound). Plasma will be isolated from trunk blood after 10,000×g centrifugation for 10 min at 4° C. The anticoagulant will be lithium-heparin. Brains would be snap frozen on dry ice. The testing procedure timeline is set forth on FIG. 7.

Those skilled in the art will recognize, or be able to ascertain using no more than routine experimentation, many equivalents to the specific embodiments described herein. Such equivalents are intended to be encompassed by the claims.

What is claimed is:

1. A method of treating PCDH19 related epilepsy comprising administering to a patient in need thereof a pharmaceutical composition comprising ganaxolone or a pharmaceutically acceptable salt thereof.

2. The method of claim 1, wherein the patient is administered ganaxolone or a pharmaceutically acceptable salt thereof twice daily.

3. The method of claim 1, wherein the patient is administered ganaxolone or a pharmaceutically acceptable salt thereof three times daily.

4. The method of claim 1, wherein the patient is administered ganaxolone or a pharmaceutically acceptable salt thereof in an amount of up to 1,800 mg/day.

5. The method of claim 1, wherein the pharmaceutical composition is an oral capsule.

6. The method of claim 1, wherein the pharmaceutical composition is an oral suspension.

7. The method of claim 1, wherein the pharmaceutical composition is an oral suspension comprising 50 mg/ml ganaxolone or a pharmaceutically acceptable salt thereof.

8. The method of claim 1, wherein the pharmaceutical composition is an oral suspension comprising 50 mg/ml ganaxolone or a pharmaceutically acceptable salt thereof and is administered three times daily.

9. The method of claim 1, wherein the pharmaceutical composition is an oral suspension comprising 50 mg/ml ganaxolone or a pharmaceutically acceptable salt thereof administered three times daily wherein the patient is administered an amount of up to 1,800 mg/day.

10. The method of claim 1, wherein the patient is administered 600 mg ganaxolone or a pharmaceutically acceptable salt thereof.

11. The method of claim 1, wherein the patient is administered 600 mg ganaxolone or a pharmaceutically acceptable salt thereof three times daily.

12. The method of claim 1, wherein the patient is administered 50 mg ganaxolone or a pharmaceutically acceptable salt thereof.

13. The method of claim 1, wherein the patient is administered 100 mg ganaxolone or a pharmaceutically acceptable salt thereof.

14. The method of claim 1, wherein the patient is administered 200 mg ganaxolone or a pharmaceutically acceptable salt thereof.

15. The method of claim 1, wherein the patient is administered 300 mg ganaxolone or a pharmaceutically acceptable salt thereof.

16. The method of claim 1, wherein the patient is administered 400 mg ganaxolone or a pharmaceutically acceptable salt thereof.

17. The method of claim 1, wherein the patient is administered 500 mg ganaxolone or a pharmaceutically acceptable salt thereof.

18. The method of claim 1, wherein the patient is administered oral capsules comprising 200-600 mg ganaxolone or a pharmaceutically acceptable salt thereof.

19. The method of claim 1, wherein the pharmaceutical composition provides reduction in the frequency of seizures.

20. The method of claim 1, wherein the pharmaceutical composition provides reduction in the frequency of seizures, the severity of seizures, or a combination thereof.

* * * * *